United States Patent
Sano et al.

(10) Patent No.: US 7,422,898 B2
(45) Date of Patent: Sep. 9, 2008

(54) NUCLEIC ACID ENCODING MONKEY GPR103

(75) Inventors: Hideki Sano, Tsukuba (JP); Hisashi Iwaasa, Tsukuba (JP); Satoshi Mashiko, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/578,592

(22) PCT Filed: Apr. 14, 2005

(86) PCT No.: PCT/JP2005/007174
§ 371 (c)(1),
(2), (4) Date: Oct. 16, 2006

(87) PCT Pub. No.: WO2005/100566
PCT Pub. Date: Oct. 27, 2005

(65) Prior Publication Data
US 2008/0009016 A1    Jan. 10, 2008

(30) Foreign Application Priority Data
Apr. 14, 2004 (JP) ............................. 2004/119564

(51) Int. Cl.
C12N 5/10   (2006.01)
C12N 15/12  (2006.01)
C12N 15/63  (2006.01)
C12N 1/21   (2006.01)
C07K 14/00  (2006.01)

(52) U.S. Cl. .................... 435/325; 435/69.1; 435/252.3; 435/320.1; 530/350; 536/23.5

(58) Field of Classification Search ........................ None
See application file for complete search history.

(56) References Cited

U.S. PATENT DOCUMENTS 6,927,041 B2 * 8/2005 Zhelnin et al. ............. 435/69.1
2004/0248790 A1 12/2004 Hinuma et al.

FOREIGN PATENT DOCUMENTS

EP    1 207 201 A1    5/2002
WO    WO 00/11015 A1  3/2000
WO    WO 02/42458 A2  5/2002

OTHER PUBLICATIONS

Baribault et al., "The G-Protein-Coupled Receptor GPR103 Regulates Bone Formation", Molecular and Cellular Biology, vol. 26(2), pp. 709-717 (2006).
Bruzzone et al., "Anatomical distribution and biochemical characterization of the novel RFamide peptide 26RFa in the human hypothalamus and spinal cord", Journal of Neurochemistry, vol. 99, pp. 616-627 (2006).
Chartrel et al., "Identification of 26RFa, a hypothalamic neuropeptide of the RFamide peptide family with orexigenic activity", PNAS, vol. 100(25), pp. 15247-15252 (2003).
do Rego et al., "Behavorial effects of 26RFamide and related peptides", Peptides, vol. 27, pp. 2715-2721 (2006).
Fukusumi et al., "A New Peptide Ligand and Its Receptor Regulating Adrenal Function in Rats", The Journal of Biological Chemistry, vol. 278(47), pp. 46387-46395 (2003).
Jiang et al., "Identification and Characterization of a Novel RF-amide Peptide Ligand for Orphan G-protein-coupled Receptor SP9155", The Journal of Biological Chemistry, vol. 278(30), pp. 27652-27657 (2003).
Kampe et al., "Effect of central administration of QRFP(26) peptide on energy balance and characterization of a second QRFP receptor in rat", Brain Research, vol. 1119, pp. 133-149 (2006).
Lee et al., "Discovery and mapping of ten novel G protein-coupled receptor genes", Gene, vol. 275, pp. 83-91 (2001).
Moriya et al., "RFamide Peptide QRFP43 Causes Obesity with Hyperphagia and Reduced Thermogensis in Mice", Endocrinology, vol. 147(6), pp. 2916-2922 (2006).
Navarro et al., "Novel role of 26RFa, a hypothalamic RFamide orexigenic peptide, as putative regulator of the gonadotropic axis", J. Physiol., vol. 573.1, pp. 237-249 (2006).
Takayasu et al., "A neuropeptide ligand of the G protein-coupled receptor GPR103 regulates feedings, behavioral arousal, and blood pressure in mice", PNAS, vol. 103(19), pp. 7438-7743 (2006).
Thuau et al., "Structural studies on 26RFa, a novel RFamide-related peptide with orexigenic activity", Peptides, vol. 26, pp. 779-789 (2005).

* cited by examiner

Primary Examiner—Christine J Saoud
Assistant Examiner—Jon M Lockard
(74) Attorney, Agent, or Firm—Heidi M. Struse; Mark R. Daniel

(57) ABSTRACT

There are provided non-human primate and rat GPR103 genes and proteins and a compound evaluation method employing the genes or proteins. There are also provided highly useful novel ligands for functional analysis of the GPR103 genes and proteins and for the compound evaluation. The nucleic acids or proteins having the sequences listed as SEQ ID NOS: 1 to 4 provide non-human primate or rat GPR103 genes and proteins and information based on the genes and proteins. The genes and proteins can be used for evaluation of compounds. The nucleic acids or proteins having the sequence listed as SEQ ID NO: 5 or 6 provide a GPR103 ligand.

4 Claims, 10 Drawing Sheets

Fig.1

```
rhesus   MVR-SYPLVCLLLPLGTCFPLLDRREPTDAMGGTGARESWADLAEGPRPHSVWGSSRWP
human    MVR-PYPLYFLPLPLGTCFPLLDRREPTDAMGGCGAGERWADLAMGPRPHSVWGSSRWL
mouse    MR-GRPLSLLLPLSACFPLLDRRGPTD-IGDIGARMNWAQLAEGHPPNSVQNP----
rat      MR-CLCSWLCLLLPLSACFPLLDRRGPTD-IGDIGARMSWVQLTEGHTPRSVQSP----
bovine   MRSPYSLFLPLGACFPVLDTEEPVDAVGGTGREMSWMDPARG-RP-FPWGSPGWP rhesus   RASQPQALLVTRGLQTSGREHAGCRFRFGRQDEGSEADDFLPAGVKASGPLGNLAEEL
human    RASQPQALLVARGLQTSGREHAGCRFRFGRQDEGSEATGFLPAAGEKTSGPLGNLAEEL
mouse    -QPQALLVAREQQASHREHTG--FRLGRQDEGSEAAGFLPADSEKASGPLGTLAEEL
rat      RPQALLVNAEEQQASREHTG--FRLGRQDSGSEATGFLPTDSEKASGPLGTLAEEL
bovine   RAPYPHALLVTAKELRASGKARAGFQLRLGRQDDGSEATGLLLGEAEKVGGLGTLAEEL rhesus   NGYSRKKGGFSFRFGRR
human    NGYSRKKGGFSFRFGRR
mouse    SSYSRRKGGFSFRFGR-
rat      SSYSRRKGGFSFRFGR-
bovine   NGYSRKKGGFSFRFGRR
```

*Fig.2*

SEQUENCE LISTING

<160> NUMBER OF SEQ ID NOS: 51

<210> SEQ ID NO 1
<211> LENGTH: 1424
<212> TYPE: DNA
<213> ORGANISM: rhesus monkey

<400> SEQUENCE: 1

```
gaggagggga ggcggcctcc tcccggttcc cccgaagccc tccctgcgcc gcggatggcc      60
aggaagtagc gggcggtggc cccgcgtccc gggagcgcac agcaatgcag gcgctcaaca     120
tcaccccgga gcagttctcc cggctgctgc gagaccacaa cctgacgcgg gagcagttca     180
tcgctctgta ccggctgcga ccgctcgtct acacccccaga gctgcctggg cgcgccaagc    240
tggccctcgt gctcaccggc gtgctcatct tcgccctggc gctctttggc aatgctctgg     300
tgttctacgt ggtgacccgc agcaaggcca tgcgcaccgt caccaacatc tttatctgct     360
ccttggcgct cagtgacctg ctcatcacct tcttctgcat cccgtcacc atgctccaga      420 acatttccga caactggctg gggggtgctt tcatttgcaa gatggtgcca tttgtccagt     480
ctaccgctgt tgtgacagaa attctcacta tgacctgcat tgctgtggaa aggcaccagg     540
gacttgtgca tccttttaaa atgaagtggc aatacaccaa ccgaagggct ttcacaatgc     600
taggtgtggt ctggctggtg gcagtcatcg taggatcacc catgtggcac gtgcaacaac     660
ttgagatcaa atatgacttc ctatatgaaa aggaacacat ttgctgctta aagagtggaa     720
ccagccctgt gcaccagaag atctacacca ccttcatcct tgtcatcctc ttcctcctgc     780
ctcttatggt gatgcttatt ctgtacagta aaattggtta tgaactttgg ataaagaaaa     840
gagttgggga tggttcagtg ctgcaaacta ttcatggaaa agaaatgtcc aaaatagcca     900
ggaagaagaa acgagctgtc attatgatgg tgacagtggt ggctctcttt gctgtgtgct     960
gggcaccatt ccatgttgtc catatgatga ttgaatacag taattttgaa aaggaatatg    1020
atgatgtcac aatcaagatg atttttgcta tcgtgcaaat tattggattt tccaactcca    1080
tctgtaatcc cattgtctat gcatttatga atgaaaactt caaaaaaaat gttttgtctg    1140
cagtttgtta ttgcatagta aacaaaacct tctctccagc acaaaggcat ggaaattcag    1200
gaattaccat gatgcagaag aaagcaaagt ttccctcag agagaatcca gtggaggaaa    1260
ccaaaggaga aacgttcagt gatggcaaca ttgaagtcaa attgtgtgag cagacaaagg    1320
agataaaaaa gctcaaacga catcttgctc tctttaggtc tgaactggct gagaattcta    1380
ctttagacag tgggcattaa ttataacaat atcttcataa ttaa                     1424
```

<210> SEQ ID NO 2
<211> LENGTH: 431
<212> TYPE: PRT
<213> ORGANISM: rhesus monkey

<400> SEQUENCE: 2

```
Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Leu Tyr Arg Leu Arg
                20                  25                  30

Pro Leu Val Tyr Thr Pro Glu Leu Pro Gly Arg Ala Lys Leu Ala Leu
            35                  40                  45

Val Leu Thr Gly Val Leu Ile Phe Ala Leu Ala Leu Phe Gly Asn Ala
        50                  55                  60

Leu Val Phe Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Thr Phe
                85                  90                  95

Phe Cys Ile Pro Val Thr Met Leu Gln Asn Ile Ser Asp Asn Trp Leu
            100                 105                 110

Gly Gly Ala Phe Ile Cys Lys Met Val Pro Phe Val Gln Ser Thr Ala
        115                 120                 125
```

Val Val Thr Glu Ile Leu Thr Met Thr Cys Ile Ala Val Glu Arg His
130                 135                 140

Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
                165                 170                 175

Gly Ser Pro Met Trp His Val Gln Gln Leu Glu Ile Lys Tyr Asp Phe
                180                 185                 190

Leu Tyr Glu Lys Glu His Ile Cys Cys Leu Glu Glu Trp Thr Ser Pro
                195                 200                 205

Val His Gln Lys Ile Tyr Thr Thr Phe Ile Leu Val Ile Leu Phe Leu
210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Gln Thr Ile
                245                 250                 255

His Gly Lys Glu Met Ser Lys Ile Ala Arg Lys Lys Arg Ala Val
                260                 265                 270

Ile Met Met Val Thr Val Val Ala Leu Phe Ala Val Cys Trp Ala Pro
                275                 280                 285

Phe His Val Val His Met Met Ile Glu Tyr Ser Asn Phe Glu Lys Glu
                290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Leu Ser Ala Val Cys Tyr Cys Ile Val
                340                 345                 350

Asn Lys Thr Phe Ser Pro Ala Gln Arg His Gly Asn Ser Gly Ile Thr
                355                 360                 365

Met Met Gln Lys Lys Ala Lys Phe Ser Leu Arg Glu Asn Pro Val Glu
370                 375                 380

Glu Thr Lys Gly Glu Thr Phe Ser Asp Gly Asn Ile Glu Val Lys Leu
385                 390                 395                 400

Cys Glu Gln Thr Lys Glu Ile Lys Lys Leu Lys Arg His Leu Ala Leu
                405                 410                 415

Phe Arg Ser Glu Leu Ala Glu Asn Ser Thr Leu Asp Ser Gly His
                420                 425                 430

<210> SEQ ID NO 3
<211> LENGTH: 1297
<212> TYPE: DNA
<213> ORGANISM: Rattus norvegicus

<400> SEQUENCE: 3
atgtcgtgga acttgaccgc ggagcagctc tcggcgctgc ttcagctgca caacctgacg    60
cgcgcgcagt tcatcgcgcg ctatgggctg cggccactgg tgctcacccc gcagctgcct   120
gcacgcgcca ggctggccct cctgcttgct ggcctgctca tctttgccct ggcgctcttc   180
ggcaacgccc tggtagtcta tgtagtgacc cgcagcaagg ccatgcgcac cgtcaccaac   240
atcttcatct gctccctggc actcagcgac ctgctcatcg ttttcttctg catccctgtc   300
accatgctcc agaacgtctc agacacctgg ctgggggggtg ccttcatttg caaaatggtg   360
ccatttgtcc agtgcactgc cgttgtgaca gaaatcctta ctatgacctg cattgctgtg   420

-continued

```
gaaaggcacc agggacttgt ccatccttt  aaaatgaagc agcagtacac caatcaaagg     480
gctttcacaa tgctaggtgt ggtgtggctg gtggccatca tcataggatc acccatgtgg     540
catgtgcaga gacttgagat taagtatgac ttcctatatg aaaaagaaca catctgctgc     600
ttggaagagt ggagcagccc cgtgcaccag aaaatctaca ccaccttcat cctcgtcacc     660
ctcttcctgc tgcctctgtt gctgctgtct gtcctctatg gaaaatcgg  ttatgagctt     720 tggatcaaga aaagagtggg agatggctca gtgctccgaa ctattcatgg aaagaaatg     780 ttcaaaatag cgagaaagaa gaagcgggct gtgatcatga tggtgacagt ggtggttctc     840
tttgctgtgt gctgggcacc tttccacgtc gttcacatga tgattgaata cagtaatttt     900
gaaaaggaat atgatgaagt cacaatcaag atgattttg  ctatagtgca ataattgga     960 tttttcaact ccatctgtaa tcccattgtt tatgcactca tgaatgaaaa cttcaaaaag    1020 aatttgtgt  ctgcagtttg ctattgtgta ataaaagaaa ccccctctcc agcacagagg    1080
catggaagct tgggagccat tgtgatgcac agaagagtga agttagctgt gggagagaat    1140
cctgtagaga tcaaggggga agcatttggg ggcagcaaca tggacatcaa gtggtgtgaa    1200
cagccagaga agaagaagaa atctcaaatg gcttcttgtc ctctttagtt ctgaattcct    1260
gagaactctg ctgtagacgt ggacactgac tgtaaca                             1297
```

<210> SEQ ID NO 4
<211> LENGTH: 415
<212> TYPE: PRT
<213> ORGANISM: Rattus norvegicus

<400> SEQUENCE: 4

```
Met Ser Trp Asn Leu Thr Ala Glu Gln Leu Ser Ala Leu Leu Gln Leu
 1               5                  10                  15

His Asn Leu Thr Arg Ala Gln Phe Ile Ala Arg Tyr Gly Leu Arg Pro
            20                  25                  30

Leu Val Leu Thr Pro Gln Leu Pro Ala Arg Ala Arg Leu Ala Leu Leu
        35                  40                  45

Leu Ala Gly Leu Leu Ile Phe Ala Leu Ala Leu Phe Gly Asn Ala Leu
    50                  55                  60

Val Val Tyr Val Val Thr Arg Ser Lys Ala Met Arg Thr Val Thr Asn
65                  70                  75                  80

Ile Phe Ile Cys Ser Leu Ala Leu Ser Asp Leu Leu Ile Val Phe Phe
                85                  90                  95

Cys Ile Pro Val Thr Met Leu Gln Asn Val Ser Asp Thr Trp Leu Gly
            100                 105                 110

Gly Ala Phe Ile Cys Lys Met Val Pro Phe Val Gln Cys Thr Ala Val
        115                 120                 125

Val Thr Glu Ile Leu Thr Met Thr Cys Ile Ala Val Glu Arg His Gln
    130                 135                 140

Gly Leu Val His Pro Phe Lys Met Lys Gln Gln Tyr Thr Asn Gln Arg
145                 150                 155                 160

Ala Phe Thr Met Leu Gly Val Val Trp Leu Val Ala Ile Ile Ile Gly
                165                 170                 175

Ser Pro Met Trp His Val Gln Arg Leu Glu Ile Lys Tyr Asp Phe Leu
            180                 185                 190

Tyr Glu Lys Glu His Ile Cys Cys Leu Glu Glu Trp Ser Ser Pro Val
        195                 200                 205

His Gln Lys Ile Tyr Thr Thr Phe Ile Leu Val Thr Leu Phe Leu Leu
```

-continued

```
                     210                 215                 220
Pro Leu Leu Leu Ser Val Leu Tyr Gly Lys Ile Gly Tyr Glu Leu
225                 230                 235                 240

Trp Ile Lys Lys Arg Val Gly Asp Gly Ser Val Leu Arg Thr Ile His
                245                 250                 255

Gly Lys Glu Met Phe Lys Ile Ala Arg Lys Lys Lys Arg Ala Val Ile
                260                 265                 270

Met Met Val Thr Val Val Leu Phe Ala Val Cys Trp Ala Pro Phe
                275                 280                 285

His Val Val His Met Met Ile Glu Tyr Ser Asn Phe Glu Lys Glu Tyr
                290                 295                 300

Asp Glu Val Thr Ile Lys Met Ile Phe Ala Ile Val Gln Ile Ile Gly
305                 310                 315                 320

Phe Phe Asn Ser Ile Cys Asn Pro Ile Val Tyr Ala Leu Met Asn Glu
                325                 330                 335

Asn Phe Lys Lys Asn Phe Val Ser Ala Val Cys Tyr Cys Val Ile Lys
                340                 345                 350

Glu Thr Pro Ser Pro Ala Gln Arg His Gly Ser Leu Gly Ala Ile Val
                355                 360                 365

Met His Arg Arg Val Lys Leu Ala Val Gly Glu Asn Pro Val Glu Ile
                370                 375                 380

Lys Gly Glu Ala Phe Gly Gly Ser Asn Met Asp Ile Lys Trp Cys Glu
385                 390                 395                 400

Gln Pro Glu Lys Lys Lys Ser Gln Met Ala Ser Cys Pro Leu
                405                 410                 415

<210> SEQ ID NO 5
<211> LENGTH: 655
<212> TYPE: DNA
<213> ORGANISM: rhesus monkey

<400> SEQUENCE: 5
cagcttgtaa ctctgcctct ctctcctctg ggtcagatgg taaggtccta cccctggtc      60 tgcctcctcc tcctgccgct gggcacctgc tttcctctac tggacagaag agagcccaca     120
gacgccatgg gtggcactgg agccagagaa agctgggccg acctggccga ggggccccga     180
ccccactctg tgtgggctc ctctcggtgg ccgagagctt cacagccaca ggccctgctt      240
gtcataacca gggggctgca gacatcgggc agagagcatg ccggctgcag gttccgcttc     300
gggaggcagg atgaaggcag tgaggccgac gacttcctcc ctgccggagg ggtgaaggcc     360
agcggcccgt tagggaacct ggctgaggag ctcaatggct acagcaggaa gaaaggcggc     420
ttcagcttcc gcttcggtcg tcggtgaagg gccaggatgc cttggaaggg tttgctgttt     480
ggactcaccc ccattgtctt cactcctgcc ttctccccca gtctcaaaga ccacgacacc     540
caggtggtgt aggcatggtt acgatgaacg atccatggaa ggacaggtta ggagggtgct     600
tgcttttgat tccaactttg ctgaagcgaa aaactaggca gtgtcaaaa aggag          655

<210> SEQ ID NO 6
<211> LENGTH: 136
<212> TYPE: PRT
<213> ORGANISM: rhesus monkey

<400> SEQUENCE: 6

Met Val Arg Ser Tyr Pro Leu Val Cys Leu Leu Leu Pro Leu Gly
1               5                   10                  15
```

```
Thr Cys Phe Pro Leu Leu Asp Arg Arg Glu Pro Thr Asp Ala Met Gly
            20                  25                  30

Gly Thr Gly Ala Arg Glu Ser Trp Ala Asp Leu Ala Glu Gly Pro Arg
        35                  40                  45

Pro His Ser Val Trp Gly Ser Arg Trp Pro Arg Ala Ser Gln Pro
    50                  55                  60

Gln Ala Leu Leu Val Ile Thr Arg Gly Leu Gln Thr Ser Gly Arg Glu
65                  70                  75                  80

His Ala Gly Cys Arg Phe Arg Phe Gly Arg Gln Asp Glu Gly Ser Glu
                85                  90                  95

Ala Asp Asp Phe Leu Pro Ala Gly Gly Val Lys Ala Ser Gly Pro Leu
                100                 105                 110

Gly Asn Leu Ala Glu Glu Leu Asn Gly Tyr Ser Arg Lys Lys Gly Gly
            115                 120                 125

Phe Ser Phe Arg Phe Gly Arg Arg
    130                 135

<210> SEQ ID NO 7
<211> LENGTH: 431
<212> TYPE: PRT
<213> ORGANISM: Homo sapiens

<400> SEQUENCE: 7

Met Gln Ala Leu Asn Ile Thr Pro Glu Gln Phe Ser Arg Leu Leu Arg
1               5                   10                  15

Asp His Asn Leu Thr Arg Glu Gln Phe Ile Ala Leu Tyr Arg Leu Arg
            20                  25                  30

Pro Leu Val Tyr Thr Pro Glu Leu Pro Gly Arg Ala Lys Leu Ala Leu
        35                  40                  45

Val Leu Thr Gly Val Leu Ile Phe Ala Leu Ala Leu Phe Gly Asn Ala
    50                  55                  60

Leu Val Phe Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Thr Phe
                85                  90                  95

Phe Cys Ile Pro Val Thr Met Leu Gln Asn Ile Ser Asp Asn Trp Leu
                100                 105                 110

Gly Gly Ala Phe Ile Cys Lys Met Val Pro Phe Val Gln Ser Thr Ala
            115                 120                 125

Val Val Thr Glu Ile Leu Thr Met Thr Cys Ile Ala Val Glu Arg His
    130                 135                 140

Gln Gly Leu Val His Pro Phe Lys Met Lys Trp Gln Tyr Thr Asn Arg
145                 150                 155                 160

Arg Ala Phe Thr Met Leu Gly Val Val Trp Leu Val Ala Val Ile Val
                165                 170                 175

Gly Ser Pro Met Trp His Val Gln Gln Leu Glu Ile Lys Tyr Asp Phe
                180                 185                 190

Leu Tyr Glu Lys Glu His Ile Cys Cys Leu Glu Glu Trp Thr Ser Pro
            195                 200                 205

Val His Gln Lys Ile Tyr Thr Thr Phe Ile Leu Val Ile Leu Phe Leu
    210                 215                 220

Leu Pro Leu Met Val Met Leu Ile Leu Tyr Ser Lys Ile Gly Tyr Glu
225                 230                 235                 240

Leu Trp Ile Lys Lys Arg Val Gly Asp Gly Ser Val Leu Arg Thr Ile
                245                 250                 255
```

His Gly Lys Glu Met Ser Lys Ile Ala Arg Lys Lys Arg Ala Val
                260                 265                 270

Ile Met Met Val Thr Val Val Ala Leu Phe Ala Val Cys Trp Ala Pro
            275                 280                 285

Phe His Val Val His Met Met Ile Glu Tyr Ser Asn Phe Glu Lys Glu
        290                 295                 300

Tyr Asp Asp Val Thr Ile Lys Met Ile Phe Ala Ile Val Gln Ile Ile
305                 310                 315                 320

Gly Phe Ser Asn Ser Ile Cys Asn Pro Ile Val Tyr Ala Phe Met Asn
                325                 330                 335

Glu Asn Phe Lys Lys Asn Val Leu Ser Ala Val Cys Tyr Cys Ile Val
            340                 345                 350

Asn Lys Thr Phe Ser Pro Ala Gln Arg His Gly Asn Ser Gly Ile Thr
        355                 360                 365

Met Met Arg Lys Lys Ala Lys Phe Ser Leu Arg Glu Asn Pro Val Glu
370                 375                 380

Glu Thr Lys Gly Glu Ala Phe Ser Asp Gly Asn Ile Glu Val Lys Leu
385                 390                 395                 400

Cys Glu Gln Thr Glu Lys Lys Lys Leu Lys Arg His Leu Ala Leu
                405                 410                 415

Phe Arg Ser Glu Leu Ala Glu Asn Ser Pro Leu Asp Ser Gly His
            420                 425                 430

<210> SEQ ID NO 8
<211> LENGTH: 433
<212> TYPE: PRT
<213> ORGANISM: Mus musculus

<400> SEQUENCE: 8

Met Gln Ala Leu Asn Ile Thr Ala Glu Gln Phe Ser Arg Leu Leu Ser
1               5                   10                  15

Ala His Asn Leu Thr Arg Glu Gln Phe Ile His Arg Tyr Gly Leu Arg
            20                  25                  30

Pro Leu Val Tyr Thr Pro Glu Leu Pro Ala Arg Ala Lys Leu Ala Phe
        35                  40                  45

Ala Leu Ala Gly Ala Leu Ile Phe Ala Leu Ala Leu Phe Gly Asn Ser
    50                  55                  60

Leu Val Ile Tyr Val Val Thr Arg Ser Lys Ala Met His Thr Val Thr
65                  70                  75                  80

Asn Ile Phe Ile Cys Ser Leu Ala Leu Ser Asp Leu Leu Ile Ala Phe
                85                  90                  95

Phe Cys Ile Pro Val Thr Met Leu Gln Asn Ile Ser Asp Lys Trp Leu
            100                 105                 110

Gly Gly Ala Phe Ile Cys Lys Met Val Pro Phe Val Gln Ser Thr Ala
        115                 120                 125

Val Val Thr Glu Ile Leu Thr Met Thr Cys Ile Ala Val Glu Arg His
    130                 135                 140

Gln Gly Leu Ile His Pro Phe Lys Met Lys Trp Gln Tyr Thr Thr Arg
145                 150                 155                 160

Arg Ala Phe Thr Ile Leu Gly Val Val Trp Leu Ala Ala Ile Ile Val
                165                 170                 175

Gly Ser Pro Met Trp His Val Gln Arg Leu Glu Ile Lys Tyr Asp Phe
            180                 185                 190

Leu Tyr Glu Lys Glu His Val Cys Cys Leu Glu Glu Trp Ala Ser Pro

-continued

```
                195                 200                 205
Met His Gln Arg Ile Tyr Thr Thr Phe Ile Leu Val Ile Leu Phe Leu
    210                 215                 220

Leu Pro Leu Val Val Met Leu Val Leu Tyr Ser Lys Ile Gly Tyr Glu
225                 230                 235                 240

Leu Trp Ile Lys Lys Arg Val Gly Asp Ser Ala Leu Gln Thr Ile
                245                 250                 255

His Gly Lys Glu Met Ser Lys Ile Ala Arg Lys Lys Arg Ala Val
            260                 265                 270

Val Met Met Val Thr Val Val Ala Leu Phe Ala Ala Cys Trp Ala Pro
        275                 280                 285

Phe His Val Val His Met Met Val Glu Tyr Ser Asn Phe Glu Lys Glu
    290                 295                 300

Tyr Asp Asp Val Thr Ile Lys Met Val Phe Ala Val Ala Gln Thr Ile
305                 310                 315                 320

Gly Phe Phe Asn Ser Ile Cys Asn Pro Phe Val Tyr Ala Phe Met Asn
                325                 330                 335

Glu Asn Phe Lys Lys Asn Phe Leu Ser Ala Val Cys Tyr Cys Ile Val
            340                 345                 350

Lys Glu Thr Phe Ser Pro Gly Gln Lys Pro Gly Asn Ser Gly Ile Ser
        355                 360                 365

Met Met Gln Lys Arg Ala Lys Leu Ser Arg Ser Gln Arg Pro Val Ala
    370                 375                 380

Glu Ala Lys Gly Asp Leu Phe Ser Asp Ala Asn Val Asp Val Lys Leu
385                 390                 395                 400

Cys Glu Gln Pro Gly Glu Lys Arg Gln Leu Lys Arg Gln Leu Ala Phe
                405                 410                 415

Phe Ser Ser Glu Leu Ser Glu Asn Ser Thr Phe Gly Ser Gly His Glu
            420                 425                 430

Leu
```

<210> SEQ ID NO 9
<211> LENGTH: 433
<212> TYPE: PRT
<213> ORGANISM: Rattus norvegicus

<400> SEQUENCE: 9

```
Met Gln Ala Leu Asn Ile Thr Ala Glu Gln Phe Ser Arg Leu Leu Ser
1               5                   10                  15

Ala His Asn Leu Thr Arg Glu Gln Phe Ile His Arg Tyr Gly Leu Arg
            20                  25                  30

Pro Leu Val Tyr Thr Pro Glu Leu Pro Ala Arg Ala Lys Val Ala Phe
        35                  40                  45

Ala Leu Ala Gly Ala Leu Ile Phe Ala Leu Ala Leu Phe Gly Asn Ser
    50                  55                  60

Leu Val Ile Tyr Val Val Thr Arg Ser Lys Ala Met Arg Thr Val Thr
65                  70                  75                  80

Asn Ile Phe Ile Cys Ser Leu Ala Leu Ser Asp Leu Leu Ile Ala Phe
                85                  90                  95

Phe Cys Ile Pro Val Thr Met Leu Gln Asn Ile Ser Asp Lys Trp Leu
            100                 105                 110

Gly Gly Ala Phe Ile Cys Lys Met Val Pro Phe Val Gln Ser Thr Ala
        115                 120                 125

Val Val Thr Glu Ile Leu Thr Met Thr Cys Ile Ala Val Glu Arg His
```

-continued

```
                130                 135                 140
Gln Gly Leu Val His Pro Phe Lys Met Lys Trp Gln Tyr Thr Thr Arg
145                 150                 155                 160

Arg Ala Phe Thr Ile Leu Gly Val Val Trp Leu Ala Ala Ile Ile Val
                165                 170                 175

Gly Ser Pro Met Trp His Val Gln Arg Leu Glu Ile Lys Tyr Asp Phe
                180                 185                 190

Leu Tyr Glu Lys Glu His Ile Cys Cys Leu Glu Glu Trp Ala Ser Pro
                195                 200                 205

Val His Gln Arg Ile Tyr Ser Thr Phe Ile Leu Val Ile Leu Phe Leu
                210                 215                 220

Leu Pro Leu Val Val Met Leu Val Leu Tyr Ser Lys Ile Gly Tyr Glu
225                 230                 235                 240

Leu Trp Ile Lys Lys Arg Val Gly Asp Ser Ser Ala Leu Gln Thr Ile
                245                 250                 255

His Gly Lys Glu Met Ser Lys Ile Ala Arg Lys Lys Arg Ala Val
                260                 265                 270

Ile Met Met Val Thr Val Val Ala Leu Phe Ala Ala Cys Trp Ala Pro
                275                 280                 285

Phe His Val Val His Met Met Val Glu Tyr Ser Asn Phe Glu Lys Glu
                290                 295                 300

Tyr Asp Asp Val Thr Ile Lys Met Val Phe Ala Val Ala Gln Thr Ile
305                 310                 315                 320

Gly Phe Phe Asn Ser Ile Cys Asn Pro Phe Val Tyr Ala Phe Met Asn
                325                 330                 335

Glu Asn Phe Lys Lys Asn Phe Leu Ser Ala Val Cys Tyr Cys Ile Val
                340                 345                 350

Lys Glu Ser Ser Ser Pro Ala Arg Lys Pro Gly Asn Ser Gly Ile Ser
                355                 360                 365

Met Met Gln Lys Arg Ala Lys Leu Ser Arg Pro Gln Arg Pro Val Glu
                370                 375                 380

Glu Thr Lys Gly Asp Thr Phe Ser Asp Ala Ser Ile Asp Val Lys Leu
385                 390                 395                 400

Cys Glu Gln Pro Arg Glu Lys Arg Gln Leu Lys Arg Gln Leu Ala Phe
                405                 410                 415

Phe Ser Ser Glu Leu Ser Glu Asn Ser Thr Phe Gly Ser Gly His Glu
                420                 425                 430

Leu
```

<210> SEQ ID NO 10
<211> LENGTH: 416
<212> TYPE: PRT
<213> ORGANISM: Mus musculus

<400> SEQUENCE: 10

```
Met Ser Trp Asn Leu Thr Ala Glu Gln Leu Ser Ala Leu Leu Arg Leu
1               5                   10                  15

His Asn Leu Thr Arg Ala Gln Phe Ile Ala His Tyr Gly Leu Arg Pro
                20                  25                  30

Leu Val Leu Thr Pro Gln Leu Pro Ala Arg Ala Arg Leu Ala Leu Leu
                35                  40                  45

Leu Val Gly Leu Leu Ile Phe Ala Leu Ala Leu Phe Gly Asn Ala Leu
                50                  55                  60

Val Val Tyr Val Val Thr Arg Ser Lys Ala Met Arg Thr Val Thr Asn
```

```
                65                  70                  75                  80
Ile Phe Ile Cys Ser Leu Ala Leu Ser Asp Leu Leu Ile Val Phe Phe
                    85                  90                  95
Cys Ile Pro Val Thr Met Leu Gln Asn Val Ser Asp Thr Trp Leu Gly
                100                 105                 110
Gly Ala Phe Ile Cys Lys Met Val Pro Phe Val Gln Cys Thr Ala Ile
                115                 120                 125
Val Thr Glu Ile Leu Thr Met Thr Cys Ile Ala Val Glu Arg His Gln
            130                 135                 140
Gly Leu Val His Pro Phe Lys Met Lys Arg Gln Tyr Thr Asn Gln Arg
145                 150                 155                 160
Ala Phe Thr Met Leu Gly Val Val Trp Leu Val Ala Ile Ile Ile Gly
                165                 170                 175
Ser Pro Met Trp His Val Gln Arg Leu Glu Ile Lys Tyr Asp Phe Leu
            180                 185                 190
Tyr Glu Lys Glu His Ile Cys Cys Leu Glu Glu Trp Ser Ser Pro Val
        195                 200                 205
His Gln Lys Ile Tyr Thr Thr Phe Ile Leu Val Thr Leu Phe Leu Leu
    210                 215                 220
Pro Leu Leu Leu Leu Ser Val Leu Tyr Gly Lys Ile Gly Tyr Glu Leu
225                 230                 235                 240
Trp Ile Lys Lys Arg Ile Gly Asp Gly Ser Val Leu Arg Thr Ile His
                245                 250                 255
Gly Lys Glu Met Phe Lys Ile Ala Arg Lys Lys Arg Ala Val Ile
                260                 265                 270
Met Met Val Thr Val Val Leu Phe Ala Val Cys Trp Ala Pro Phe
            275                 280                 285
His Ile Val His Met Met Ile Glu Tyr Ser Asn Phe Glu Lys Glu Tyr
        290                 295                 300
Asp Glu Val Thr Ile Lys Met Ile Phe Ala Ile Val Gln Ile Ile Gly
305                 310                 315                 320
Phe Phe Asn Ser Ile Cys Asn Pro Ile Ile Tyr Ala Leu Met Asn Glu
                325                 330                 335
Asn Phe Lys Lys Asn Phe Val Ser Ala Val Cys Tyr Cys Ile Val Lys
                340                 345                 350
Glu Thr Pro Ser Ser Ala Arg Lys His Gly Ser Ser Gly Ala Met Val
            355                 360                 365
Met His Arg Arg Ala Lys Leu Ala Ala Arg Glu Asn Pro Val Glu Ile
        370                 375                 380
Lys Gly Glu Ala Phe Gly Gly Ser Asn Ile Asp Ile Lys Trp Cys Glu
385                 390                 395                 400
Gln Pro Glu Lys Lys Lys Arg Arg Ser Lys Val Ala Ser Cys Pro Leu
                405                 410                 415

<210> SEQ ID NO 11
<211> LENGTH: 136
<212> TYPE: PRT
<213> ORGANISM: Homo sapiens

<400> SEQUENCE: 11

Met Val Arg Pro Tyr Pro Leu Ile Tyr Phe Leu Phe Leu Pro Leu Gly
1               5                   10                  15
Ala Cys Phe Pro Leu Leu Asp Arg Arg Glu Pro Thr Asp Ala Met Gly
            20                  25                  30
```

```
Gly Leu Gly Ala Gly Glu Arg Trp Ala Asp Leu Ala Met Gly Pro Arg
            35                  40                  45

Pro His Ser Val Trp Gly Ser Ser Arg Trp Leu Arg Ala Ser Gln Pro
    50                  55                  60

Gln Ala Leu Leu Val Ile Ala Arg Gly Leu Gln Thr Ser Gly Arg Glu
65                  70                  75                  80

His Ala Gly Cys Arg Phe Arg Phe Gly Arg Gln Asp Glu Gly Ser Glu
                85                  90                  95

Ala Thr Gly Phe Leu Pro Ala Ala Gly Glu Lys Thr Ser Gly Pro Leu
            100                 105                 110

Gly Asn Leu Ala Glu Glu Leu Asn Gly Tyr Ser Arg Lys Lys Gly Gly
        115                 120                 125

Phe Ser Phe Arg Phe Gly Arg Arg
    130                 135

<210> SEQ ID NO 12
<211> LENGTH: 124
<212> TYPE: PRT
<213> ORGANISM: Mus musculus

<400> SEQUENCE: 12

Met Arg Gly Phe Arg Pro Leu Leu Ser Leu Leu Pro Leu Ser Ala
1               5                   10                  15

Cys Phe Pro Leu Leu Asp Arg Arg Gly Pro Thr Asp Ile Gly Asp Ile
                20                  25                  30

Gly Ala Arg Met Asn Trp Ala Gln Leu Ala Glu Gly His Pro Pro Asn
            35                  40                  45

Ser Val Gln Asn Pro Gln Pro Gln Ala Leu Leu Val Val Ala Arg Glu
    50                  55                  60

Gln Gln Ala Ser His Arg Glu His Thr Gly Phe Arg Leu Gly Arg Gln
65                  70                  75                  80

Asp Gly Ser Ser Glu Ala Ala Gly Phe Leu Pro Ala Asp Ser Glu Lys
                85                  90                  95

Ala Ser Gly Pro Leu Gly Thr Leu Ala Glu Glu Leu Ser Ser Tyr Ser
            100                 105                 110

Arg Arg Lys Gly Gly Phe Ser Phe Arg Phe Gly Arg
        115                 120

<210> SEQ ID NO 13
<211> LENGTH: 124
<212> TYPE: PRT
<213> ORGANISM: Rattus norvegicus

<400> SEQUENCE: 13

Met Arg Cys Leu Cys Ser Trp Leu Cys Leu Leu Pro Leu Ser Ala
1               5                   10                  15

Cys Phe Pro Leu Leu Asp Arg Arg Gly Pro Thr Asp Ile Gly Asp Ile
                20                  25                  30

Gly Ala Arg Met Ser Trp Val Gln Leu Thr Glu Gly His Thr Pro Arg
            35                  40                  45

Ser Val Gln Ser Pro Arg Pro Gln Ala Leu Leu Val Val Ala Lys Glu
    50                  55                  60

Gln Gln Ala Ser Arg Arg Glu His Thr Gly Phe Arg Leu Gly Arg Gln
65                  70                  75                  80

Asp Ser Gly Ser Glu Ala Thr Gly Phe Leu Pro Thr Asp Ser Glu Lys
                85                  90                  95
```

```
Ala Ser Gly Pro Leu Gly Thr Leu Ala Glu Glu Leu Ser Ser Tyr Ser
            100                 105                 110
Arg Arg Lys Gly Gly Phe Ser Phe Arg Phe Gly Arg
            115                 120
```

<210> SEQ ID NO 14
<211> LENGTH: 134
<212> TYPE: PRT
<213> ORGANISM: bovine

<400> SEQUENCE: 14

```
Met Arg Ser Pro Tyr Ser Leu Pro Tyr Leu Leu Phe Leu Pro Leu Gly
1               5                   10                  15
Ala Cys Phe Pro Val Leu Asp Thr Glu Glu Pro Val Asp Ala Val Gly
            20                  25                  30
Gly Thr Gly Arg Glu Met Ser Trp Met Asp Pro Ala Arg Gly Arg Pro
        35                  40                  45
Phe Pro Trp Gly Ser Pro Gly Trp Pro Arg Ala Pro Tyr Pro His Ala
    50                  55                  60
Leu Leu Val Thr Ala Lys Glu Leu Arg Ala Ser Gly Lys Ala Arg Ala
65                  70                  75                  80
Gly Phe Gln Leu Arg Leu Gly Arg Gln Asp Asp Gly Ser Glu Ala Thr
                85                  90                  95
Gly Leu Leu Leu Gly Glu Ala Glu Lys Val Gly Gly Leu Leu Gly Thr
            100                 105                 110
Leu Ala Glu Glu Leu Asn Gly Tyr Ser Arg Lys Lys Gly Gly Phe Ser
            115                 120                 125
Phe Arg Phe Gly Arg Arg
    130
```

<210> SEQ ID NO 15
<211> LENGTH: 33
<212> TYPE: DNA
<213> ORGANISM: Artificial
<220> FEATURE:
<223> OTHER INFORMATION: synthetic polynucleotide

<400> SEQUENCE: 15
ataggatcct cccgcgcggc tgactccaga gta                          33

<210> SEQ ID NO 16
<211> LENGTH: 35
<212> TYPE: DNA
<213> ORGANISM: Artificial
<220> FEATURE:
<223> OTHER INFORMATION: synthetic polynucleotide

<400> SEQUENCE: 16
acagcggccg ctctttgggt tacaatctga agggc                        35

<210> SEQ ID NO 17
<211> LENGTH: 20
<212> TYPE: DNA
<213> ORGANISM: Artificial
<220> FEATURE:
<223> OTHER INFORMATION: synthetic polynucleotide

<400> SEQUENCE: 17
taatacgact cactataggg                                         20

<210> SEQ ID NO 18

```
<211> LENGTH: 18
<212> TYPE: DNA
<213> ORGANISM: Artificial
<220> FEATURE:
<223> OTHER INFORMATION: synthetic polynucleotide

<400> SEQUENCE: 18
ggagctgaca cggaagat                                                 18

<210> SEQ ID NO 19
<211> LENGTH: 17
<212> TYPE: DNA
<213> ORGANISM: Artificial
<220> FEATURE:
<223> OTHER INFORMATION: synthetic polynucleotide

<400> SEQUENCE: 19
gggagcagtt catcgct                                                  17

<210> SEQ ID NO 20
<211> LENGTH: 20
<212> TYPE: DNA
<213> ORGANISM: Artificial
<220> FEATURE:
<223> OTHER INFORMATION: synthetic polynucleotide

<400> SEQUENCE: 20
ctcgtgctca ccggcgtgct                                               20

<210> SEQ ID NO 21
<211> LENGTH: 19
<212> TYPE: DNA
<213> ORGANISM: Artificial
<220> FEATURE:
<223> OTHER INFORMATION: synthetic polynucleotide

<400> SEQUENCE: 21
cagtcatcgt aggatcacc                                                19

<210> SEQ ID NO 22
<211> LENGTH: 20
<212> TYPE: DNA
<213> ORGANISM: Artificial
<220> FEATURE:
<223> OTHER INFORMATION: synthetic polynucleotide

<400> SEQUENCE: 22
ttctcctctg tctgttcaca                                               20

<210> SEQ ID NO 23
<211> LENGTH: 20
<212> TYPE: DNA
<213> ORGANISM: Artificial
<220> FEATURE:
<223> OTHER INFORMATION: synthetic polynucleotide

<400> SEQUENCE: 23
aatgacagct cgtttcttct                                               20

<210> SEQ ID NO 24
<211> LENGTH: 20
<212> TYPE: DNA
<213> ORGANISM: Artificial
<220> FEATURE:
<223> OTHER INFORMATION: synthetic polynucleotide

<400> SEQUENCE: 24
```

-continued caatgcaggt catagtgagg　　　　　　　　　　　　　　　　　　　　　　20

<210> SEQ ID NO 25
<211> LENGTH: 20
<212> TYPE: DNA
<213> ORGANISM: Artificial
<220> FEATURE:
<223> OTHER INFORMATION: synthetic polynucleotide

<400> SEQUENCE: 25
agcacgccgg tgagcacgag　　　　　　　　　　　　　　　　　　　　　　20

<210> SEQ ID NO 26
<211> LENGTH: 19
<212> TYPE: DNA
<213> ORGANISM: Artificial
<220> FEATURE:
<223> OTHER INFORMATION: synthetic polynucleotide

<400> SEQUENCE: 26
ggtgatccta cgatgactg　　　　　　　　　　　　　　　　　　　　　　　19

<210> SEQ ID NO 27
<211> LENGTH: 36
<212> TYPE: DNA
<213> ORGANISM: Artificial
<220> FEATURE:
<223> OTHER INFORMATION: synthetic polynucleotide

<400> SEQUENCE: 27
ataggatcct tggtgagttg cgcttggcca cgtgtg　　　　　　　　　　　　　36

<210> SEQ ID NO 28
<211> LENGTH: 38
<212> TYPE: DNA
<213> ORGANISM: Artificial
<220> FEATURE:
<223> OTHER INFORMATION: synthetic polynucleotide

<400> SEQUENCE: 28
acagcggccg cggctgggac gaccgaggct ccaagaca　　　　　　　　　　　　38

<210> SEQ ID NO 29
<211> LENGTH: 20
<212> TYPE: DNA
<213> ORGANISM: Artificial
<220> FEATURE:
<223> OTHER INFORMATION: synthetic polynucleotide

<400> SEQUENCE: 29
taatacgact cactataggg　　　　　　　　　　　　　　　　　　　　　　20

<210> SEQ ID NO 30
<211> LENGTH: 18
<212> TYPE: DNA
<213> ORGANISM: Artificial
<220> FEATURE:
<223> OTHER INFORMATION: synthetic polynucleotide

<400> SEQUENCE: 30
ggagctgaca cggaagat　　　　　　　　　　　　　　　　　　　　　　　18

<210> SEQ ID NO 31
<211> LENGTH: 20
<212> TYPE: DNA

```
<213> ORGANISM: Artificial
<220> FEATURE:
<223> OTHER INFORMATION: synthetic polynucleotide

<400> SEQUENCE: 31
catgctggct gcagattccg                                               20

<210> SEQ ID NO 32
<211> LENGTH: 20
<212> TYPE: DNA
<213> ORGANISM: Artificial
<220> FEATURE:
<223> OTHER INFORMATION: synthetic polynucleotide

<400> SEQUENCE: 32
tcactgcctt cgtcctgcct                                               20

<210> SEQ ID NO 33
<211> LENGTH: 37
<212> TYPE: DNA
<213> ORGANISM: Artificial
<220> FEATURE:
<223> OTHER INFORMATION: synthetic polynucleotide

<400> SEQUENCE: 33
ataggatccg gtcaaggcgc ctaccgaacc cagcatg                            37

<210> SEQ ID NO 34
<211> LENGTH: 35
<212> TYPE: DNA
<213> ORGANISM: Artificial
<220> FEATURE:
<223> OTHER INFORMATION: synthetic polynucleotide

<400> SEQUENCE: 34
acagcggccg caacaggtcc tcattctgaa gacac                              35

<210> SEQ ID NO 35
<211> LENGTH: 20
<212> TYPE: DNA
<213> ORGANISM: Artificial
<220> FEATURE:
<223> OTHER INFORMATION: synthetic polynucleotide

<400> SEQUENCE: 35
taatacgact cactataggg                                               20

<210> SEQ ID NO 36
<211> LENGTH: 18
<212> TYPE: DNA
<213> ORGANISM: Artificial
<220> FEATURE:
<223> OTHER INFORMATION: synthetic polynucleotide

<400> SEQUENCE: 36
ggagctgaca cggaagat                                                 18

<210> SEQ ID NO 37
<211> LENGTH: 20
<212> TYPE: DNA
<213> ORGANISM: Artificial
<220> FEATURE:
<223> OTHER INFORMATION: synthetic polynucleotide

<400> SEQUENCE: 37
tcaccttctt ctgcattccc                                               20
```

<210> SEQ ID NO 38
<211> LENGTH: 20
<212> TYPE: DNA
<213> ORGANISM: Artificial
<220> FEATURE:
<223> OTHER INFORMATION: synthetic polynucleotide

<400> SEQUENCE: 38
aaaatctaca ccaccttcat                                          20

<210> SEQ ID NO 39
<211> LENGTH: 20
<212> TYPE: DNA
<213> ORGANISM: Artificial
<220> FEATURE:
<223> OTHER INFORMATION: synthetic polynucleotide

<400> SEQUENCE: 39
gcatggaagc ttgggagcca                                          20

<210> SEQ ID NO 40
<211> LENGTH: 20
<212> TYPE: DNA
<213> ORGANISM: Artificial
<220> FEATURE:
<223> OTHER INFORMATION: synthetic polynucleotide

<400> SEQUENCE: 40
cccccaaatg cttcccctttt                                         20

<210> SEQ ID NO 41
<211> LENGTH: 20
<212> TYPE: DNA
<213> ORGANISM: Artificial
<220> FEATURE:
<223> OTHER INFORMATION: synthetic polynucleotide

<400> SEQUENCE: 41
agctcataac cgattttccc                                          20

<210> SEQ ID NO 42
<211> LENGTH: 22
<212> TYPE: DNA
<213> ORGANISM: Artificial
<220> FEATURE:
<223> OTHER INFORMATION: synthetic polynucleotide

<400> SEQUENCE: 42
atgagcaggt cgctgagtgc ca                                       22

<210> SEQ ID NO 43
<211> LENGTH: 23
<212> TYPE: DNA
<213> ORGANISM: Artificial
<220> FEATURE:
<223> OTHER INFORMATION: synthetic polynucleotide

<400> SEQUENCE: 43
tctttggcaa ctctctggtc atc                                      23

<210> SEQ ID NO 44
<211> LENGTH: 23
<212> TYPE: DNA
<213> ORGANISM: Artificial
<220> FEATURE:

-continued

<210> SEQ ID NO 44
<211> LENGTH: 23
<212> TYPE: DNA
<213> ORGANISM: Artificial
<220> FEATURE:
<223> OTHER INFORMATION: synthetic polynucleotide

<400> SEQUENCE: 44
cagaagaagg caatgagcag atc                                              23

<210> SEQ ID NO 45
<211> LENGTH: 23
<212> TYPE: DNA
<213> ORGANISM: Artificial
<220> FEATURE:
<223> OTHER INFORMATION: synthetic polynucleotide

<400> SEQUENCE: 45
tgcgcaccgt caccaacatc ttc                                              23

<210> SEQ ID NO 46
<211> LENGTH: 20
<212> TYPE: DNA
<213> ORGANISM: Artificial
<220> FEATURE:
<223> OTHER INFORMATION: synthetic polynucleotide

<400> SEQUENCE: 46
tctccctctg agtgcctgct                                                  20

<210> SEQ ID NO 47
<211> LENGTH: 20
<212> TYPE: DNA
<213> ORGANISM: Artificial
<220> FEATURE:
<223> OTHER INFORMATION: synthetic polynucleotide

<400> SEQUENCE: 47
gcctgtgctg tggattttga                                                  20

<210> SEQ ID NO 48
<211> LENGTH: 24
<212> TYPE: DNA
<213> ORGANISM: Artificial
<220> FEATURE:
<223> OTHER INFORMATION: synthetic polynucleotide

<400> SEQUENCE: 48
cagacatcgg tgacatcgga gcca                                             24

<210> SEQ ID NO 49
<211> LENGTH: 43
<212> TYPE: PRT
<213> ORGANISM: rhesus monkey
<220> FEATURE:
<221> NAME/KEY: MISC_FEATURE
<222> LOCATION: (1)..(1)
<223> OTHER INFORMATION: Xaa is Pyr, Pyroglutamic acid.
<220> FEATURE:
<221> NAME/KEY: MOD_RES
<222> LOCATION: (43)..(43)
<223> OTHER INFORMATION: AMIDATION

<400> SEQUENCE: 49

Xaa Asp Glu Gly Ser Glu Ala Asp Asp Phe Leu Pro Ala Gly Gly Val
1               5                   10                  15

Lys Ala Ser Gly Pro Leu Gly Asn Leu Ala Glu Glu Leu Asn Gly Tyr
            20                  25                  30

Ser Arg Lys Lys Gly Gly Phe Ser Phe Arg Phe
        35                  40

```
<210> SEQ ID NO 50
<211> LENGTH: 26
<212> TYPE: PRT
<213> ORGANISM: rhesus monkey
<220> FEATURE:
<221> NAME/KEY: MOD_RES
<222> LOCATION: (26)..(26)
<223> OTHER INFORMATION: AMIDATION

<400> SEQUENCE: 50

Ala Ser Gly Pro Leu Gly Asn Leu Ala Glu Glu Leu Asn Gly Tyr Ser
1               5                   10                  15

Arg Lys Lys Gly Gly Phe Ser Phe Arg Phe
            20                  25

<210> SEQ ID NO 51
<211> LENGTH: 43
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Pyr, Pyroglutamic acid.
<220> FEATURE:
<221> NAME/KEY: MOD_RES
<222> LOCATION: (43)..(43)
<223> OTHER INFORMATION: AMIDATION

<400> SEQUENCE: 51

Xaa Asp Glu Gly Ser Glu Ala Thr Gly Phe Leu Pro Ala Ala Gly Glu
1               5                   10                  15

Lys Thr Ser Gly Pro Leu Gly Asn Leu Ala Glu Glu Leu Asn Gly Tyr
            20                  25                  30

Ser Arg Lys Lys Gly Gly Phe Ser Phe Arg Phe
        35                  40
```

NUCLEIC ACID ENCODING MONKEY GPR103

This application is the National Stage of International Application No. PCT/JP2005/007174, filed on Apr. 13, 2005, which claims the benefit of JP Application No. 2004-119564, filed Apr. 14, 2004.

TECHNICAL FIELD

The present invention relates to novel monkey and rat GPR103 genes and proteins, and to a compound evaluation method using the genes or proteins. The invention further relates to GPR103 ligand proteins.

BACKGROUND ART

Most hormones, neurotransmitters or bioactive substances that regulate body functions transmit signals to target cells via guanosine triphosphate-binding protein (hereinafter, "G protein")-coupled receptors present on cell membranes, whereby their unique functions are exhibited. Such receptors have a seven membrane spanning structure in common and form the G protein-coupled receptor superfamily.

Several hundred different G protein-coupled receptors have already been isolated to date, but some still remain to be isolated. Many orphan receptors with unknown ligands also exist.

Isolation of these receptors and ligands and elucidation of their functions will lead to understanding of their physiological function in the body, and should also permit screening of agonists or antagonists capable of controlling their function, thereby contributing to the development of new pharmaceuticals.

GPR103 (also known as SP9155 or AQ27) is one type of G protein-coupled receptor, and the human GPR103 gene and protein have been isolated by PCR (Polymerase Chain Reaction) using sequence information obtained from an EST and genomic DNA database search based on the amino acid sequence of different G protein-coupled receptors (Non-patent document 1). Also, the amino acid sequence of human GPR103 protein has been disclosed in Patent document 1.

Mouse GPR103 is disclosed in Patent document 2 and Patent document 3. In addition, rat GPR103 is disclosed in Patent document 3.

GPR103 has high homology to orexin, neuropeptide FF and cholecystokinin receptors and was predicted to exhibit similar function to these molecules, but its actual function was unknown. However, Ying Jiang et al. later discovered a peptide that functions as its ligand (Non-patent document 2, Patent document 4), and it has been suggested that it helps to induce secretion of aldosterone in rat adrenal zona glomerulosa (Non-patent document 3).

Candidate compounds for development of therapeutic and diagnostic agents are evaluated by their physiological effects in rodents and primates. This is because candidate compounds exhibit different drug effects in different animal species, and evaluation in primates that are most closely related to humans contributes to efficient development of therapeutic and diagnostic agents with low toxicity.

[Patent document 1] WO0011015
[Patent document 2] WO02002042458
[Patent document 3] Japanese Unexamined Patent Publication No. 2004-000113
[Patent document 4] Japanese Unexamined Patent Publication No. 2001-136981
[Non-patent document 1] Gene, Vol. 275, 83(2001)
[Non-patent document 2] Journal of Biological Chemistry, Vol. 278, 27652(2003).
[Non-patent document 3] Journal of Biological Chemistry, Vol. 278, 46387(2003).

DISCLOSURE OF THE INVENTION (Problems to be Solved by the Invention)

However, a non-human primate GPR103 gene has not yet been isolated, and therefore it has not been possible to evaluate therapeutic or diagnostic agents using such a gene.

It is an object of the present invention, which has been accomplished in light of the aforementioned problem of the prior art, to provide non-human primate GPR103 genes and proteins. It is another object of the invention to provide a compound evaluation method using the genes or proteins. It is yet another object of the invention to provide highly useful novel ligands for functional analysis of the GPR103 genes and proteins and for the aforementioned compound evaluation.

(Means for Solving the Problems)

As a result of much diligent research directed toward achieving the objects stated above, the present inventors have succeeded in isolating novel monkey and rat GPR103 genes (SEQ ID NO: 1 and 3) and in isolating the monkey-derived GPR103 ligand preproP518/QRFP (SEQ ID NO: 5), and have also succeeded in designing and synthesizing proteins QRFP43 (SEQ ID NO: 49) and QRFP26 (SEQ ID NO: 50) having GPR103 ligand activity based on monkey QRFP, and in evaluating ligands by binding experiments using these molecules, whereupon the present invention has been completed.

Specifically, a nucleic acid of the invention is characterized by containing the nucleotide sequence listed as SEQ ID NO: 1 or 3. Here, "containing the nucleotide sequence listed as SEQ ID NO: 1 or 3" means that the nucleotide sequence includes an additional nucleotide sequence, such as a sequence necessary for modification of the gene which may be a vector linker sequence or a restriction enzyme cleavage site or the like that can be used for gene recombination.

A nucleic acid of the invention is also characterized by consisting of the nucleotide sequence listed as SEQ ID NO: 1 or 3.

A nucleic acid of the invention is further characterized by coding for a protein consisting of the amino acid sequence listed as SEQ ID NO: 2 or 4.

These nucleic acids of the invention can yield information regarding non-human primate and rat GPR103 genes and proteins and their sequences, and permit construction of GPR103 model systems as targets mainly for human drugs.

A gene of the invention is also characterized by comprising nucleic acid that hybridizes with nucleic acid containing the nucleotide sequence listed as SEQ ID NO: 1 under stringent conditions. Using such a gene allows detection of genes with high homology to the monkey GPR103 gene.

A gene of the invention is also characterized by comprising nucleic acid that hybridizes with nucleic acid containing the nucleotide sequence listed as SEQ ID NO: 3 under stringent conditions. Using such a gene allows detection or isolation of genes with high homology to the rat GPR103 gene.

The invention also encompasses an expression vector containing the aforementioned nucleic acid or gene. Using such a vector allows manipulation of GPR103 on the genetic level and expression of its recombinant protein.

The invention further encompasses a host cell containing the aforementioned expression vector. Using such a host cell permits cellular level research for evaluation of ligands such as compounds or peptides.

A protein of the invention is characterized by containing the amino acid sequence listed as SEQ ID NO: 2 or 4. Here, "containing the amino acid sequence listed as SEQ ID NO: 2 or 4" means that the amino acid sequence is linked with an additional amino acid sequence such as a reporter protein or another amino acid sequence necessary for use in detection and evaluation of the protein.

A protein of the invention is further characterized by consisting of the amino acid sequence listed as SEQ ID NO: 2 or 4.

A protein of the invention is still further characterized by containing the amino acid sequence listed as SEQ ID NO: 2 or 4 with a substitution, deletion, addition or insertion of one or more amino acids and having the activity of GPR103 protein.

These proteins of the invention can yield information regarding non-human primate and rat GPR103 genes and proteins and their sequences, and permit construction of GPR103 model systems as targets mainly for human drugs.

The invention further encompasses antibodies for the aforementioned proteins. Using such an antibody can produce an antigen-antibody reaction with GPR103 protein, thereby allowing detection of the protein or diagnosis using GPR103 protein as the target.

The compound evaluation method of the invention is characterized by comprising a step of preparing cells having the GPR103 gene transferred therein and expressing GPR103 protein, a step of contacting the cells with a test compound and a step of detecting specific binding of the test compound with GPR103.

The compound evaluation method of the invention is also characterized by comprising a step of preparing cells having the GPR103 gene transferred therein and expressing GPR103 protein, a step of contacting the cells with a test compound, a step of assaying the activity of an intracellular signal transducer induced by the contact and a step of comparing that activity with activity of the intracellular signal transducer in the absence of contact with the test compound.

The compound evaluation method of the invention is also characterized by comprising a step of contacting a test compound with GPR103 protein and a step of detecting change in activity of the protein caused by the contact.

The compound evaluation method as described above allows evaluation of a compound that binds GPR103 protein (for example, an agonist or antagonist).

The invention also encompasses any compound selected by the compound evaluation method of the invention. Such a compound can lead to a diagnostic or therapeutic agent for a disease associated with GPR103.

In the compound evaluation method of the invention, the GPR103 is preferably monkey GPR103. Using monkey GPR103 will allow evaluation of compounds under conditions more closely resembling those in the human body.

A nucleic acid of the invention is also characterized by containing the nucleotide sequence listed as SEQ ID NO: 5. Here, "containing the nucleotide sequence listed as SEQ ID NO: 5" means that the nucleotide sequence includes an additional nucleotide sequence, such as a sequence necessary for modification of the gene which may be a vector linker sequence or a restriction enzyme cleavage site or the like that can be used for gene recombination.

A nucleic acid of the invention is also characterized by consisting of the nucleotide sequence listed as SEQ ID NO: 5.

A nucleic acid of the invention is further characterized by coding for a protein consisting of the amino acid sequence listed as SEQ ID NO: 6.

These nucleic acids provide nucleic acids coding for GPR103 ligand protein (QRFP) and information relating to the nucleic acids, while also providing ligands that are highly useful for functional analysis of the GPR103 genes and proteins and for the aforementioned compound evaluation method.

A gene of the invention is still further characterized by comprising nucleic acid that hybridizes with nucleic acid having the nucleotide sequence listed as SEQ ID NO: 5 under stringent conditions. This gene can be used for detection or isolation of genes with high homology to QRFP.

A protein of the invention is further characterized by containing the amino acid sequence listed as SEQ ID NO: 6. Here, "containing the amino acid sequence listed as SEQ ID NO: 6" means that the amino acid sequence is linked with an additional amino acid sequence such as a reporter protein or another amino acid sequence necessary for use in detection and evaluation of the protein.

A protein of the invention is still further characterized by consisting of the amino acid sequence listed as SEQ ID NO: 6.

A protein of the invention is still further characterized by containing the amino acid sequence listed as SEQ ID NO: 6 with a substitution, deletion, addition or insertion of one or more amino acids and having the activity of GPR103 ligand protein (QRFP).

A protein of the invention is still further characterized by consisting of the amino acid sequence listed as SEQ ID NO: 49 or 50.

The invention further encompasses antibodies for the aforementioned proteins. Such antibodies can be used to produce an antigen-antibody reaction with QRFP protein, thereby allowing detection of the protein or diagnosis using the protein as the target.

These nucleic acids, proteins and antibodies provide GPR103 ligand proteins (QRFP) and information relating to the proteins, while also providing ligands that are highly useful for functional analysis of the GPR103 genes and proteins and for the compound evaluation method of the invention.

EFFECT OF THE INVENTION

The nucleic acids, genes, proteins and antibodies of the invention provide non-human primate and rat GPR103 genes and proteins and information relating to their sequences, as well as GPR103 ligand proteins (QRFP) and information relating to the proteins. The compound evaluation method of the invention permits evaluation and development of compounds as therapeutic and diagnostic agents for diseases associated with physiological function of GPR103.

BRIEF EXPLANATION OF THE DRAWINGS

FIG. 1 shows a comparison between the amino acid sequence of human GPR103 (SEQ ID NO: 7), monkey GPR103 (SEQ ID NO: 2), mouse GPR103 (SEQ ID NO: 8), rat GPR103 (SEQ ID NO: 9), mouse GPR103*b* (SEQ ID NO: 10) and rat GPR103*B* (SEQ ID NO: 4).

FIG. 2 shows a comparison between the amino acid sequences of monkey QRFP (SEQ ID NO: 6), human QRFP (SEQ ID NO: 11), mouse QRFP (SEQ ID NO: 12), rat QRFP (SEQ ID NO: 13), and bovine QRFP (SEQ ID NO: 14).

BEST MODE FOR CARRYING OUT THE INVENTION

Figure 3:
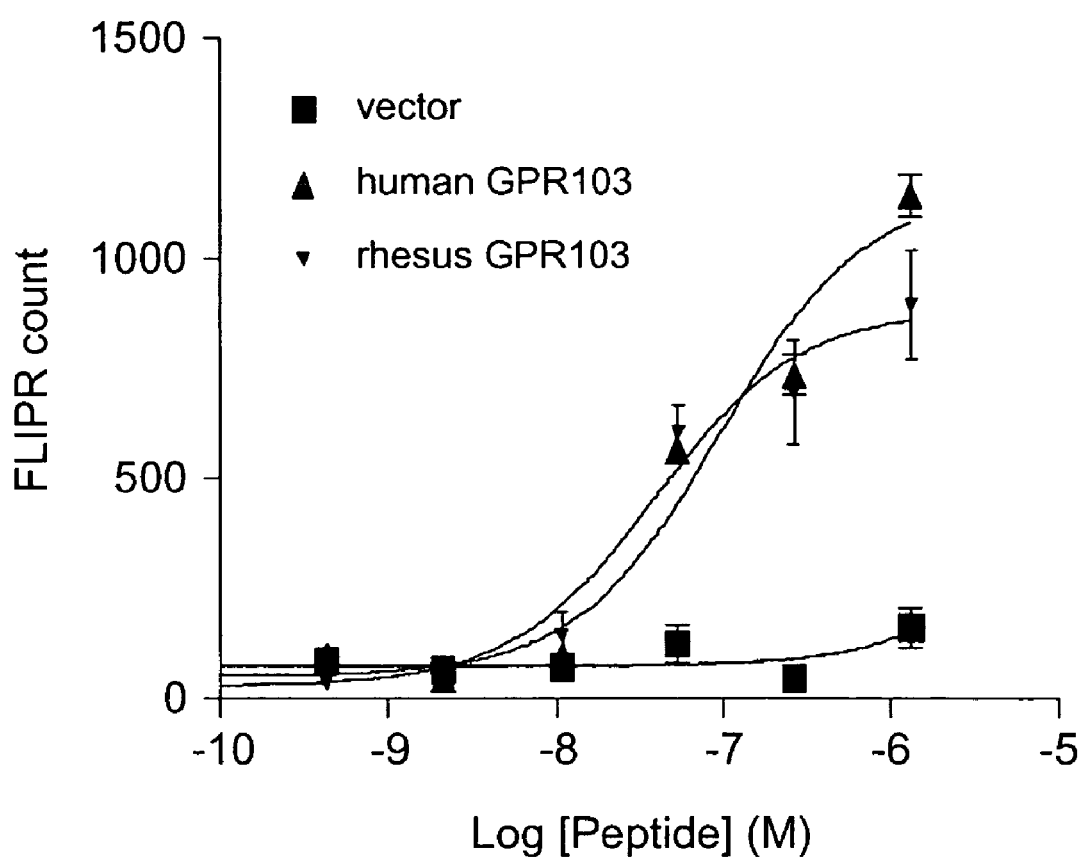
FIG. 3 is a graph showing intracellular calcium ion concentration increasing activity exhibited by different concentrations of QRFP for human and monkey GPR103-expressing 293T cells.

Preferred embodiments of the invention will now be described in detail.

The term "nucleic acid" according to the invention refers to, for example, DNA, RNA or modified DNA or RNA, and is preferably DNA. The DNA may be either genomic DNA or cDNA, and either single-stranded or double-stranded.

The term "isolated" according to the invention means that the nucleic acid or protein contains substantially no cellular substances or culturing medium in the case of production by recombinant DNA technology, or contains substantially no precursor substances or other substances in the case of chemical synthesis.

The phrase "hybridizes . . . under stringent conditions" as used according to the invention means that two nucleic acid fragments hybridize together under the hybridization conditions described in Molecular Cloning: A Laboratory Manual, 2nd Edition, Cold Spring Harbor (1989), 9.47-9.62 and 11.45-11.61. More specifically, for example, the conditions are hybridization with 6.0×SSC at approximately 45° C. followed by rinsing with 2.0×SSC at 50° C. For selection of stringency, the salt concentration during the rinsing step, for example at 50° C., may be selected from approximately 2.0× SSC as low stringency to approximately 0.2×SSC as high stringency. Also, the temperature for the rinsing step may be increased from room temperature (approximately 22° C.) as low stringency conditions to approximately 65° C. for high stringency conditions.

The monkey (rhesus monkey) GPR103 according to the invention will now be explained.

The monkey GPR103 gene (SEQ ID NO: 1) of the invention has a 1293 base open reading frame (bases 105-1397 of the nucleic acid listed as SEQ ID NO: 1), and codes for a protein of 431 amino acids (SEQ ID NO: 2).

The method of cloning the monkey GPR103 gene is not particularly restricted, and specifically there may be mentioned a method of amplifying full-length cDNA by 5'-RACE or 3'-RACE based on nucleic acid sequence information from the monkey GPR103 gene or a gene having high homology to the gene, and a method of screening a cDNA library constructed with a suitable vector (plasmid vector, bacteriophage, etc.) using a nucleic acid fragment of the monkey GPR103 gene.

The homology between the monkey GPR103 gene and human GPR103 gene is approximately 97% in the coding region, with a difference of 35 bases. The nucleic acid of the invention includes the nucleotide sequence listed as SEQ ID NO: 1 having a substitution, deletion, insertion or addition of one or more bases. The number of substituted, deleted, inserted or added bases is preferably 1-34, more preferably 1-30, even more preferably 1-20, particularly preferably 1-15 and most preferably 1-10. Based on homology, the nucleic acid also preferably has more than 97% homology, more preferably at least 98% homology and most preferably at least 99% homology to the nucleotide sequence listed as SEQ ID NO: 1. The nucleic acid also preferably codes for a protein with biological activity, and more preferably it codes for a protein having activity as GPR103 (for example, signal transducing activity as a G protein-coupled receptor).

The nucleic acid may be obtained by isolation of nucleic acid that hybridizes with nucleic acid containing the nucleotide sequence listed as SEQ ID NO: 1 according to the invention under stringent conditions. There are no particular restrictions on the animal species from which the nucleic acid is derived, but specifically a non-human primate-derived GPR103 gene is preferred, among which there may be mentioned as specific examples rhesus monkey, cynomolgus monkey, Japanese monkey, squirrel monkey, green monkey, anubis baboon and common marmoset GPR103 genes.

The homology between monkey GPR103 (SEQ ID NO: 2) and human GPR103 (SEQ ID NO: 7) on the amino acid level is 98.1%, with a difference of 8 amino acids. The protein of the invention includes that of SEQ ID NO: 2 having a substitution, deletion, insertion or addition of one or more amino acids. The number of substituted, deleted, inserted or added bases is preferably 1-7 amino acids, more preferably 1-5 amino acids and most preferably 1-3 amino acids. Based on homology, the protein preferably has at least 98.2%, more preferably at least 98.5% and most preferably at least 99% homology to the amino acid sequence listed as SEQ ID NO: 2.

There are no particular restrictions on the method of preparing the monkey GPR103, and specifically there may be mentioned a method of introducing the isolated monkey GPR103 gene into an expression vector and transferring it into a host cell such as an animal cell, an insect cell or an *E. coli*, expressing the recombinant protein and purifying it.

The invention also encompasses the protein having the amino acid sequence listed as SEQ ID NO: 2 or its mutant. As mutants there may be mentioned proteins having the amino acid sequence listed as SEQ ID NO: 2 with a substitution or deletion of 1 or more and no more than 7 amino acids, or having an addition or insertion of one or more amino acids. Such a mutant protein preferably has biological activity, and more preferably it has activity as GPR103 (for example, signal transducing activity as a G protein-coupled receptor).

The invention also includes an expression vector containing the following nucleic acids and gene.

1. Isolated nucleic acid containing the nucleotide sequence listed as SEQ ID NO: 1.
2. Isolated nucleic acid consisting of the nucleotide sequence listed as SEQ ID NO: 1.
3. Isolated nucleic acid coding for a protein consisting of the amino acid sequence listed as SEQ ID NO: 2.

4. A monkey GPR103 gene consisting of nucleic acid that hybridizes with nucleic acid containing the nucleotide sequence listed as SEQ ID NO: 1 under stringent conditions.

The aforementioned expression vector is not particularly restricted so long as it is a well-known vector to those skilled in the art, and as examples there may be mentioned pcDNA3.1, pBlueBacHis2, pCI-neo, pcDNAI, pMC1 neo, pXT1, pSG5, pEF1/V5-HisB, pCR2.1, pET11, λgt11 and pCR3.1.

Here, "containing the nucleotide sequence listed as SEQ. ID NO: 1" in 1. above means that the nucleotide sequence includes an added sequence necessary for modification of the gene which may be a vector linker sequence or a restriction enzyme cleavage site or the like that can be used for gene recombination.

The invention further includes a host cell containing the aforementioned expression vector. Such a host cell is not particularly restricted so long as it is a well-known cell to those skilled in the art, and it may be an animal cell, an insect cell, a plant cell or a microbe. As specific examples of such a cell there may be mentioned COS1, COS7, CHO, NIH/3T3, 293, Raji, CV11, C1271, MRC-5, CPAE, L-M(TK−), HeLa, 293T and Sf9.

The invention also includes an antibody for the protein having the amino acid sequence listed as SEQ ID NO: 2 or its mutant. The antibody may be prepared using the protein or a partial peptide thereof as antigen, and it may be either a monoclonal antibody or polyclonal antibody. Depending on the amino acid sequence of the epitope, the antibody may react not only with monkey GPR103 but also with GPR103 of different animal species, but if an antibody is to be prepared having selectivity only for monkey GPR103, a region of GPR103 with low homology between monkey and other animal species may be used as peptide antigen to prepare a monoclonal antibody in order to obtain an antibody having the desired specificity.

The rat GPR103b of the invention will now be explained.

The rat GPR103b gene (SEQ ID NO: 3) of the invention has a 1245 base open reading frame (bases 1-1245 of the nucleic acid listed as SEQ ID NO: 3), and codes for a protein of 415 amino acids (SEQ ID NO: 4). As mentioned above, a rat GPR103 gene has already been isolated but its nucleotide sequence differs from that of the rat GPR103b gene of the invention. For convenience, the known rat GPR103 will be referred to as rat GPR103 or rat GPR103a, and the rat GPR103 of the invention will be referred to as rat GPR103b.

There are no particular restrictions on the method of cloning the rat GPR103b gene, and specifically there may be mentioned a method of amplifying full-length cDNA by 5'-RACE or 3'-RACE based on nucleic acid sequence information from the rat GPR103b gene or a gene having high homology to the gene, and a method of screening a cDNA library constructed with a suitable vector (plasmid vector, bacteriophage, etc.) using a nucleic acid fragment of the rat GPR103b gene.

The homology between the rat GPR103b gene and rat GPR103 gene is 81% in the coding region, with a difference of 240 bases.

The homology between the rat GPR103b gene and human GPR103 gene is approximately 84% in the coding region, with a difference of 191 bases. The nucleic acid of the invention includes the nucleotide sequence listed as SEQ ID NO: 1 having a substitution, deletion, insertion or addition of one or more bases. The number of substituted, deleted, inserted or added bases is preferably 1-190, more preferably 1-150, even more preferably 1-100, particularly preferably 1-50 and most preferably 1-30. Based on homology, the nucleic acid also preferably has at least 85%, more preferably at least 90%, even more preferably at least 95% and most preferably at least 98% homology to the nucleotide sequence listed as SEQ ID NO: 1. The nucleic acid also preferably codes for a protein with biological activity, and more preferably it codes for a protein having activity as GPR103 (for example, signal transducing activity as a G protein-coupled receptor).

The nucleic acid may be obtained by isolation of nucleic acid that hybridizes with nucleic acid containing the nucleotide sequence listed as SEQ ID NO: 3 according to the invention under stringent conditions.

As mentioned above, rat GPR103b consists of 415 amino acids, and the homology to rat GPR103 on the amino acid level is 79%, with a difference of 88 amino acids.

The homology between rat GPR103b and human GPR103 (SEQ ID NO: 7) is 83%, with a difference of 71 amino acids.

The protein of the invention includes that of SEQ ID NO: 4 having a substitution, deletion, insertion or addition of one or more amino acids. The number of substituted, deleted, inserted or added bases is preferably 1-70 amino acids, more preferably 1-50 amino acids, even more preferably 1-30 amino acids and most preferably 1-10 amino acids. Based on homology, the protein preferably has at least 84%, more preferably at least 90%, even more preferably at least 95% and most preferably at least 98% homology to the amino acid sequence listed as SEQ ID NO: 4. Such a mutant protein preferably has biological activity, and more preferably it has activity as GPR103 (for example, signal transducing activity as a G protein-coupled receptor).

There are no particular restrictions on the method of preparing the rat GPR103b, and specifically there may be mentioned a method of introducing the isolated rat GPR103b gene into an expression vector and transferring it into a host cell such as an animal cell, an insect cell or an *E. coli*, expressing the recombinant protein and purifying it.

The invention also includes an expression vector containing the following nucleic acids and gene.

1. Isolated nucleic acid containing the nucleotide sequence listed as SEQ ID NO: 3.
2. Isolated nucleic acid consisting of the nucleotide sequence listed as SEQ ID NO: 3.
3. Isolated nucleic acid coding for a protein consisting of the amino acid sequence listed as SEQ ID NO: 4.
4. A rat GPR103 gene consisting of nucleic acid that hybridizes with nucleic acid containing the nucleotide sequence listed as SEQ ID NO: 3 under stringent conditions.

The aforementioned expression vector is not particularly restricted so long as it is a well-known vector to those skilled in the art, and as examples there may be mentioned pcDNA3.1, pBlueBacHis2, pCI-neo, pcDNAI, pMC1, pXT1, pSG5, pEF1/V5-HisB, pCR2.1, pET11, λgt11 and pCR3.1.

Here, "containing the nucleotide sequence listed as SEQ ID NO: 3" in 1. above means that the nucleotide sequence includes an added sequence necessary for modification of the gene which may be a vector linker sequence or a restriction enzyme cleavage site or the like that can be used for gene recombination.

The invention further includes a host cell containing the aforementioned expression vector. Such a host cell is not particularly restricted so long as it is a well-known cell to those skilled in the art, and it may be an animal cell, an insect cell, a plant cell or a microbe. As specific examples of such a cell there may be mentioned COS1, COS7, CHO, NIH/3T3, 293, Raji, CV11, C1271, MRC-5, CPAE, L-M(TK−), HeLa, 293T and Sf9.

The invention also includes an antibody for the protein having the amino acid sequence listed as SEQ ID NO: 4 or its mutant. The antibody may be prepared using the protein or a partial peptide thereof as antigen, and it may be either a monoclonal antibody or polyclonal antibody. Depending on the amino acid sequence of the epitope, the antibody may react not only with rat GPR103b but also with GPR103 of different animal species, but if an antibody is to be prepared having selectivity only for rat GPR103b, a region of GPR103 with low homology between rat and other animal species may be used as peptide antigen to prepare a monoclonal antibody in order to obtain an antibody having the desired specificity.

Uses of a nucleic acid having the nucleotide sequence listed as SEQ ID NO: 1 or 3 or a protein having the amino acid sequence listed as SEQ ID NO: 2 or 4 will be enumerated and explained next.

(1) Compound Evaluation

A nucleic acid or protein of the invention may be used for evaluation of compounds that have action on GPR103. The method of detecting action on GPR103 may be a method of detecting specific binding of a test compound on the receptor, a method of detecting a change in gene or protein expression level by contact with a test compound, and a method of detecting intracellular signal transduction activity via GPR103 induced by the contact. These will now be explained in order.

Specifically, the compound evaluation method of the invention is characterized by comprising a step of preparing cells having the GPR103 gene transferred therein and expressing the receptor, a step of contacting the cells with a test compound and a step of detecting specific binding of the test compound with the receptor.

A second compound evaluation method of the invention is characterized by comprising a step of preparing cells having the GPR103 gene transferred therein and expressing the receptor, a step of contacting the cells with a test compound, a step of assaying the activity of an intracellular signal transducer induced by the contact and a step of comparing that activity with activity of the intracellular signal transducer in the absence of contact with the test compound.

The test compound is not particularly restricted, and as examples there may be mentioned proteins, peptides, non-peptide compounds and artificially synthesized compounds.

The cells expressing the GPR103 gene may be prepared by a method known to those skilled in the art, and while no particular restrictions are placed on the method, the following method may be mentioned as an example. Specifically, it may be prepared by cloning nucleic acid having the nucleotide sequence listed as SEQ ID NO: 1 according to the invention or a nucleic acid comprising a portion thereof in an expression vector containing a suitable promoter and transcription regulating element, and introducing a vector comprising the cloned nucleic acid into a host cell. There are no particular restrictions on the vector so long as it can be used as an expression vector, and as examples there may be mentioned pcDNA3.1, pBlueBacHis2, pCI-neo, pcDNAI, pMC1, pXT1, pSG5, pEF1/V5-HisB, pCR2.1, pET11, λgt11 and pCR3.1.

The expression vector into which the nucleic acid of the invention has been introduced is then transferred into a host cell. The host cell is not particularly restricted so long as it is ordinarily used for gene expression, and it may be an animal cell, an insect cell, an plant cell or a microbe, among which there may be mentioned as specific examples COS1, COS7, CHO, NIH/3T3, 293, Raji, CV11, C1271, MRC-5, CPAE, HeLa, 293T and Sf9. The method of transferring the expression vector into the host cell is not particularly restricted so long as it is a publicly known method, and specifically there may be mentioned electroporation, the calcium phosphate method, the DEAE-dextran method, lipofection and the gene gun method.

The GPR103-expressing cell prepared in this manner is then contacted with a test compound. The contacting method is not particularly restricted, and as an example there may be mentioned a method of contact in a solution such as an aqueous solution or buffer solution.

Binding of the test compound with the receptor expressed on the cell surface can be detected, for example, via labeling attached to the bound compound (for example, detection of binding by radioactivity or fluorescent intensity), or it may be detected using an indicator based on signal transduction into the cell by binding of the test compound to the receptor on the cell membrane such as, for example, G protein activation, change in calcium ion ($Ca^{2+}$) or cAMP concentration, phospholipase C activation, pH change, receptor internalization or the like.

There may also be used as an indicator the expression level or activity of a molecule involved in a different signal transduction induced by the aforementioned signal transduction. When the expression level is used as the indicator, there are no particular restrictions on the method of assaying the expression level, and for example, there may be mentioned Northern blotting, Western blotting or a DNA chip. When the object of expression detection is nucleic acid, the "expression level" according to the invention means the absolute or relative amount of a gene, or its transcription product, coding for a protein in the signal transduction pathway that includes the GPR103 protein. When the object of expression detection is protein, the "expression level" means the absolute or relative amount of translation product of the gene coding for the protein in the signal transduction pathway that includes the GPR103 protein. When the activity of a molecule involved in signal transduction is used as the indicator, the activity assay method is not particularly restricted, and a suitable method may be selected depending on the nature of the molecule to be assayed.

On the other hand, the isolated GPR103 protein can also be used directly for evaluation of the compound. That is, such a method involves contact of the test compound with the GPR103 protein followed by detection of the change in GPR103 protein activity caused by the contact.

There are no particular restrictions on the method of contact, and as specific examples there may be mentioned a method of accomplishing contact by mixing in a solution such as a buffer solution (phosphate buffer or the like), and a method of immobilizing the GPR103 protein on a membrane and contacting it with a test compound on the membrane.

Change in the activity of the GPR103 protein caused by the contact is then detected. The protein activity assay method may be appropriately selected depending on the nature of the protein used, and as a specific example there may be mentioned a method of using binding activity of a GPR103 protein ligand (for example, QRFP) as the indicator.

There are no particular restrictions on a method of using ligand binding activity as the indicator, and as an example there may be mentioned a method of assaying binding activity based on measuring affinity of the test compound for a membrane on which GPR103 protein has been immobilized. The compound used here may be labeled with a radioactive isotope or the like to facilitate detection. The method of detecting binding activity may also be a method in which a radioactive isotope-labeled ligand that competes with the test compound for binding to GPR103 protein is detected, in which case the test compound does not need to be labeled.

Thus, if as a result of detecting the compound by the compound evaluation method of the invention, the binding activity of a ligand in the presence of a test compound has a lower value than the binding activity in the absence of the test compound (control), the test compound is judged as having activity of inhibiting binding between the GPR103 protein of the invention and the ligand. Such compounds include compounds having activity of inducing signal transduction into the cell upon binding with the receptor (agonists) and compounds having no such activity (antagonists). An agonist has the same physiological activity as the ligand for the receptor and its analogs, while an antagonist inhibits the physiological activity of the ligand for the receptor and its analogs. Thus, such agonists and antagonists are useful as pharmaceutical compositions for treatment of diseases caused by abnormalities in signal transduction systems that include the GPR103 protein of the invention.

The compound evaluation method of the invention can be used for screening of substances that promote or inhibit intracellular signal transduction that follows binding of a test compound to GPR103 protein. That is, evaluation of multiple test compounds by this method can be performed for selection of compounds that function as agonists or antagonists. If, as a result of such selection, the change in intracellular signal transduction with the ligand or its analog in the absence of the test compound is inhibited, the test compound is judged to be a compound that inhibits intracellular signal transduction upon binding of the test compound to the GPR103 of the invention. Conversely, if the test compound augments intracellular signal transduction, the compound is judged to be a compound that promotes intracellular signal transduction upon binding of the test compound to the GPR103 of the invention. When a compound selected by such a screening method is to be used as a pharmaceutical, it may be useful for prevention or treatment of various conditions associated with GPR103 or its ligand, and specifically, for example, circulatory system disorders such as angina, acute/congestive heart failure, myocardial infarction, hypertension, kidney disease, electrolyte imbalance and vasospasm, nervous system disorders such as bulimia, anorexia, depression, anxiety, convulsion, epilepsy, dementia, pain, alcohol dependency, drug discontinuation withdrawal symptoms, circadian rhythm alteration, ataxia, memory disturbance, sleep disorder and cognitive impairment, metabolic disorders such as obesity, diabetes, hormone secretion imbalances, gout and fatty liver, reproductive disorders such as infertility, preterm delivery and sex function disorders, as well as gastrointestinal diseases, respiratory diseases, inflammatory conditions, hypercholesterolemia, hyperlipidemia, atherosclerosis and glaucoma.

The compound evaluation method of the invention as described above also allows evaluation of ligands used for PET (Positron Emission Tomography). PET is a non-invasive method for observing biological function by labeling a substance found in the body such as water, oxygen, glucose or amino acids, or a ligand for a target receptor, with a radioactive substance and administering it to the body, and the method is used for research and clinical study. A feature of PET is that it allows function-specific imaging dependent on the ligand used as the tracer, and development of new tracers is indispensable for elucidation of unknown biological functions and diagnosis of disease. For the compound evaluation method of the present invention, the PET ligand candidate substance may be used as the test compound to allow in vitro evaluation of the substance.

(2) Probe used for Hybridization

A portion of nucleic acid according to the invention or the entire nucleic acid may be used as a hybridization probe for detection of the GPR103 gene. The detection is not limited to detection of the GPR103 gene in a specimen of biological tissue or cells, but also may be applied for cloning of the GPR103 gene or a gene having high homology to the gene. Also, the nucleic acid may be used as a probe for identification of gene expression distribution by examining gene expression in different tissues.

When the nucleic acid is used as a probe, there are no particular restrictions on the method of hybridization, and as examples there may be mentioned Southern hybridization, Northern hybridization, colony hybridization, dot hybridization, fluorescence in situ hybridization (FISH), in situ hybridization (ISH) and the DNA chip method.

When the nucleic acid is used as a probe for hybridization, a nucleic acid with a length of at least 20 contiguous bases is required, and the length is preferably a minimum of 40 bases, more preferably 60 bases and most preferably 80 bases. The probe may also be labeled for detection if necessary. Specifically, it may be labeled with a radioactive isotope such as $^{32}P$, $^{14}C$, $^{125}I$, $^{3}H$ or $^{35}S$, or it may be labeled with biotin, a fluorescent dye, an enzyme, a metal colloid or the like.

The conditions for hybridization when the nucleic acid is used as a hybridization probe may be selected as appropriate by a person skilled in the art depending on the length of the probe and the manner of the gene as the target of hybridization, and it may be carried out, for example, with reference to Molecular Cloning: A Laboratory Manual, 2nd Edition, Cold Spring Harbor (1989), 9.47-9.62 and 11.45-11.61. More specifically, the conditions may be hybridization with 6.0×SSC at approximately 45° C. followed by rinsing with 2.0×SSC at 50° C. For selection of stringency, the salt concentration for the rinsing step may be selected from about 2.0×SSC, 50° C. for low stringency to about 0.2×SSC, 50° C. for high stringency. Also, the temperature for the rinsing step may be increased from room temperature (approximately 22° C.) for low stringency conditions to approximately 65° C. for high stringency conditions.

(3) Primers used for PCR

The method of detecting the GPR103 gene may be the Polymerase Chain Reaction (PCR) using portions of the nucleotide sequence listed as SEQ ID NO: 1 of the invention as primers.

The lengths of the primers used may be appropriately selected based on their nucleotide sequences and the nucleotide sequence of the isolated gene, but they will generally be 10-60 and preferably 15-30 contiguous bases long.

Finally, the GPR103 ligand (QRFP: pyroglutamylated arginine-phenylalanine-amide peptide) will be explained.

The GPR103 ligand gene of the invention (preproP518/QRFP) (SEQ ID NO: 5) has a 408 base open reading frame (bases 37-444 of the nucleic acid listed as SEQ ID NO: 5), and codes for a protein composed of 136 amino acids (SEQ ID NO: 6).

There are no particular restrictions on the method of cloning the monkey GPR103 ligand gene, and as specific examples there may be mentioned a method of amplifying full-length cDNA by 5'-RACE or 3'-RACE based on nucleic acid sequence information from the monkey GPR103 ligand gene or a gene having high homology to the gene, and a method of screening a cDNA library constructed with a suitable vector (plasmid vector, bacteriophage, etc.) using a nucleic acid fragment of the monkey GPR103 ligand gene.

The homology between the monkey GPR103 ligand gene and the human GPR103 ligand gene is approximately 92% in the coding region, with a difference of 32 bases. The nucleic acid of the invention includes the nucleotide sequence listed as SEQ ID NO: 5 having a substitution, deletion, insertion or addition of one or more bases. The number of substituted, deleted, inserted or added bases is preferably 1-31, more preferably 1-20, even more preferably 1-10, particularly preferably 1-5 and most preferably 1-3. Based on homology, the nucleic acid also preferably at least 93% and most preferably at least 95% homology to the nucleotide sequence listed as SEQ ID NO: 5. The nucleic acid also preferably codes for a protein with biological activity, and more preferably it codes for a protein having activity as GPR103 ligand.

The nucleic acid may be obtained by isolation of nucleic acid that hybridizes with nucleic acid containing the nucleotide sequence listed as SEQ ID NO: 5 according to the invention under stringent conditions. There are no particular restrictions on the animal species from which the nucleic acid is derived, and specifically a non-human primate-derived GPR103 ligand gene is preferred, among which there may be mentioned as specific examples rhesus monkey, cynomolgus monkey, Japanese monkey, squirrel monkey, green monkey, anubis baboon and common marmoset GPR103 ligand genes.

The homology between monkey GPR103 ligand and human GPR103 ligand (SEQ ID NO: 11) on the amino acid level is 87.5%, with a difference of 17 amino acids. The protein of the invention includes that of SEQ ID NO: 6 having a substitution, deletion, insertion or addition of one or more amino acids. The number of substituted, deleted, inserted or added bases is preferably 1-16 amino acids, more preferably 1-10 amino acids, even more preferably 1-5 amino acids and most preferably 1-3 amino acids. Based on homology, the protein preferably has at least 88%, more preferably at least 90%, even more preferably at least 95% and most preferably at least 98% homology to the amino acid sequence listed as SEQ ID NO: 6. Such a protein preferably has biological activity, and more preferably it has activity as GPR103 ligand.

There are no particular restrictions on the method of preparing the monkey GPR103, and specifically there may be mentioned a method of introducing the isolated monkey GPR103 gene into an expression vector and transferring it into a host cell such as an animal cell, an insect cell or an *E. coli*, expressing the recombinant protein and purifying it.

The invention also encompasses the protein having the amino acid sequence listed as SEQ ID NO: 6 or its mutant. As mutants there may be mentioned proteins having the amino acid sequence listed as SEQ ID NO: 6 with a substitution or deletion of 1 or more and no more than 16 amino acids, or having an addition or insertion of one or more amino acids. Such a mutant protein preferably has biological activity, and more preferably it has activity as a GPR103 ligand (for example, the ability to bind to a G protein-coupled receptor).

The invention also includes a protein consisting of the amino acid sequence listed as SEQ ID NO: 49 or 50. These proteins may be purified by isolating nucleic acid coding for the proteins by the method described above and expressing it in a host cell, or they may be synthesized using a commercially available peptide synthesizer.

The invention also includes an antibody for the protein having the amino acid sequence listed as SEQ ID NO: 6 or its mutant, and for the protein consisting of the amino acid sequence listed as SEQ ID NO: 49 or 50. The antibody may be prepared using GPR103 ligand protein of the invention or a partial peptide thereof as antigen, and it may be either a monoclonal antibody or polyclonal antibody. Depending on the amino acid sequence of the epitope, the antibody may react not only with monkey GPR103 ligand but also with GPR103 ligands of different animal species, but if an antibody is to be prepared having selectivity only for monkey GPR103 ligand, a region of GPR103 with low homology between monkey and other animal species may be used as peptide antigen to prepare a monoclonal antibody in order to obtain an antibody having the desired specificity.

The monkey GPR103 ligand of the invention may be administered to restore normal function of GPR103 protein for diseases involving reduced expression of GPR103 in the body.

When the monkey GPR103 ligand of the invention is to be used as a drug, it may be useful for prevention or treatment of various conditions associated with GPR103, and specifically, for example, circulatory system disorders such as angina, acute/congestive heart failure, myocardial infarction, hypertension, kidney disease, electrolyte imbalance and vasospasm, nervous system disorders such as bulimia, anorexia, depression, anxiety, convulsion, epilepsy, dementia, pain, alcohol dependency, drug discontinuation withdrawal symptoms, circadian rhythm alteration, ataxia, memory disturbance, sleep disorder and cognitive impairment, metabolic disorders such as obesity, diabetes, hormone secretion imbalances, gout and fatty liver, reproductive disorders such as infertility, preterm delivery and sex function disorders, as well as gastrointestinal diseases, respiratory diseases, inflammatory conditions, hypercholesterolemia, hyperlipidemia, atherosclerosis and glaucoma.

EXAMPLES

The present invention will now be explained in greater detail based on examples, with the understanding that these examples are in no way limitative on the invention.

Example 1

(Isolation of Rhesus Monkey GPR103 Gene)

Two oligo DNA primers hBG29F2 (SEQ ID NO: 15) and hBG29R1 (SEQ ID NO: 16) were designed based on the nucleotide sequences of 5' and 3' non-translated regions of the human GPR103 gene (GenBank Accession No. BD270051).

The mRNA was purified from rhesus monkey brain tissue using a FastTrack 2.0 mRNA Separation Kit (Invitrogen Corp.), and a SuperScript III: First Strand Synthesis System (Invitrogen Corp.) was used to synthesize cDNA, which was used as template with the primers for PCR reaction comprising 40 cycles each consisting of 94° C., 10 seconds (denaturing reaction)/60° C., 30 seconds (annealing)/68° C., 1 min 30 seconds (extension reaction). The obtained PCR amplification product was digested with restriction endonucleases BamHI and NotI, and cloned in pEF1/V5-HisB plasmid vector (Invitrogen Corp.).

Five clones were randomly selected from among clones obtained by five independent PCR reactions, and the ten primers T7, BGHreverse, monBG29-1, monBG29-2, monBG29-3, monBG29-4, monBG29-5, monBG29-6, monBG29-21 and monBG29-31 (SEQ ID NOS: 17-26) were used to determine the nucleotide sequences by the dye terminator method. Comparison of the nucleotide sequences of the five clones revealed the nucleotide sequence of the rhesus monkey GPR103 gene.

The rhesus monkey GPR103 gene has a 1128 base open reading frame (bases 105 to 1397 of the nucleotide sequence listed as SEQ ID NO: 1). The amino acid sequence (431 residues) predicted from each open reading frame is listed as SEQ ID NO: 2.

Upon comparing the amino acid sequence of rhesus monkey GPR103 with that of human GPR103 (GenPept Accession No. BAC98938), very high homology of 98% was found (423 of 431 residues identical), confirming that the nucleotide sequence of the cloned gene codes for rhesus monkey GPR103 receptor.

When the regions of human GPR103 gene expression were examined, high expression was found in the hypothalamus and pons, and relatively high expression was also found in the other regions of the brain.

Figure 1:
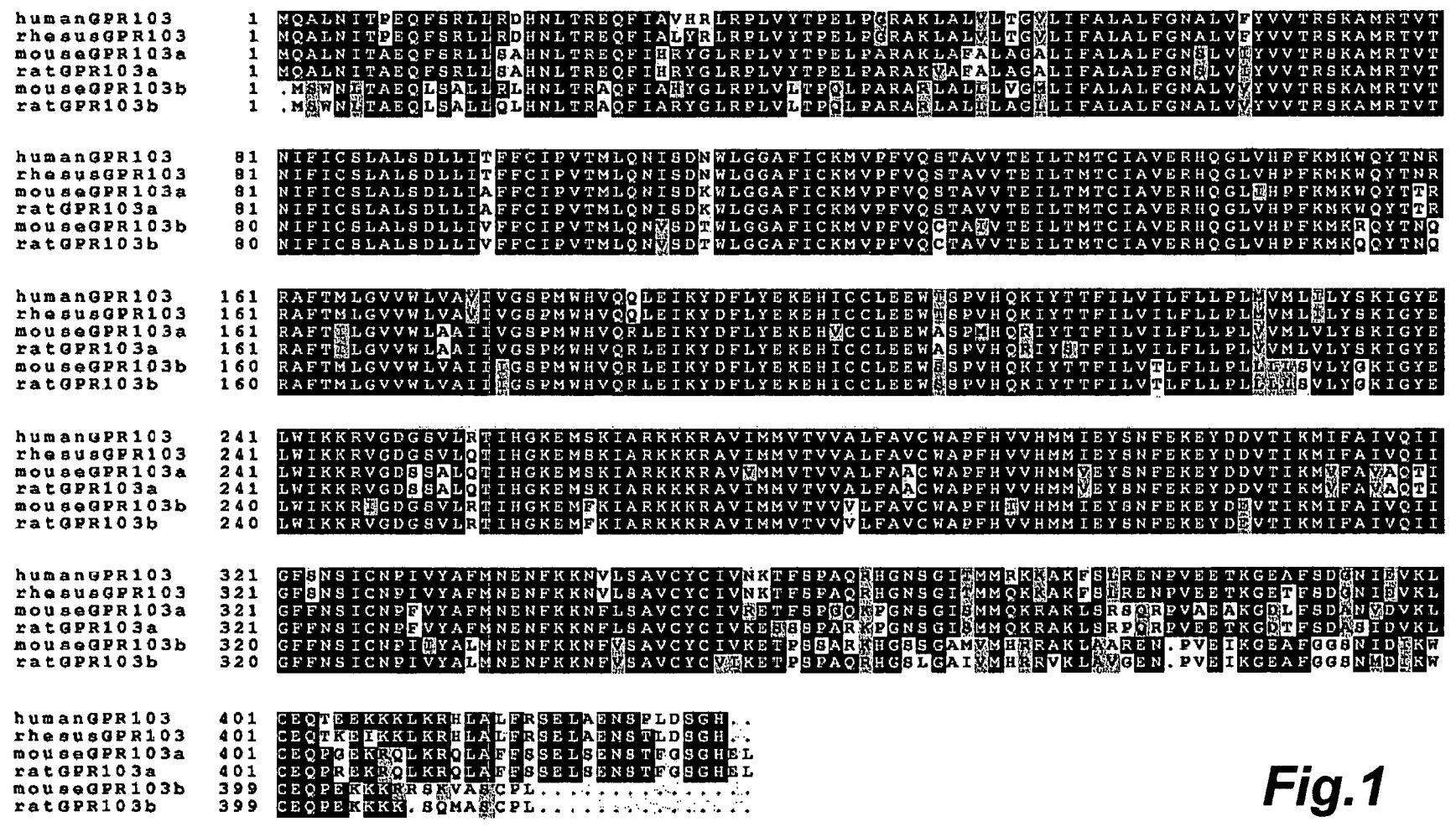

FIG. 1 shows a comparison between the amino acid sequences of human GPR103 (SEQ ID NO: 7), monkey GPR103 (SEQ ID NO: 2), mouse GPR103 (SEQ ID NO: 8), rat GPR103 (SEQ ID NO: 9), mouse GPR103b (SEQ ID NO: 10) and rat GPR103b (SEQ ID NO: 4).

The nucleotide sequences of the primers used for this example are shown below.

```
                                              (SEQ ID NO: 15)
hBG29F2:    ATAGGATCCTCCCGCGCGGCTGACTCCAGAGTA (SEQ ID NO: 16)
hBG29R1:    ACAGCGGCCGCTCTTTGGGTTACAATCTGAAGGGC (SEQ ID NO: 17)
T7:         TAATACGACTCACTATAGGG (SEQ ID NO: 18)
BGHreverse: GGAGCTGACACGGAAGAT (SEQ ID NO: 19)
monBG29-1   GGGAGCAGTTCATCGCT (SEQ ID NO: 20)
monBG29-2:  CTCGTGCTCACCGGCGTGCT (SEQ ID NO: 21)
monBG29-3:  CAGTCATCGTAGGATCACC (SEQ ID NO: 22)
monBG29-4:  TTCTCCTCTGTCTGTTCACA (SEQ ID NO: 23)
monBG29-5:  AATGACAGCTCGTTTCTTCT (SEQ ID NO: 24)
monBG29-6:  CAATGCAGGTCATAGTGAGG (SEQ ID NO: 25)
monBG29-21: AGCACGCCGGTGAGCACGAG (SEQ ID NO: 26)
monBG29-31  GGTGATCCTACGATGACTG
```

EXAMPLE 2

(Isolation of Rhesus Monkey preproQRFP Gene)

Two oligo DNA primers hQRFPF2 (SEQ ID NO: 27) and hQRFPR1 (SEQ ID NO: 28) were designed based on the nucleotide sequences of 5' and 3' non-translated regions of the human preproQRFP gene (GenBank Accession No. NT_035014).

The mRNA was purified from rhesus monkey brain tissue using a FastTrack 2.0 mRNA Separation Kit (Invitrogen Corp.), and a SuperScript III: First Strand Synthesis System (Invitrogen Corp.) was used to synthesize cDNA, which was used as template with the primers for PCR reaction comprising 40 cycles each consisting of 94° C., 10 seconds (denaturing reaction)/60° C., 30 seconds (annealing)/68° C., 1 min 30 seconds (extension reaction). The obtained PCR amplification product was digested with restriction endonucleases BamHI and NotI, and cloned in pEF 1/V5-HisB plasmid vector (Invitrogen Corp.). Eight clones were randomly selected from among clones obtained by eight independent PCR reactions, and the four primers T7, BGHreverse, hQRFP-1 and hQRFP-2 (SEQ ID NOS: 29-32) were used to determine the nucleotide sequences by the dye terminator method. Comparison of the nucleotide sequences of the five clones revealed the nucleotide sequence of the rhesus monkey preproQRFP gene.

The rhesus monkey preproQRFP gene has a 408 base open reading frame (bases 37 to 444). The amino acid sequence (136 residues) predicted from each open reading frame is listed as SEQ ID NO: 6.

Upon comparing the amino acid sequence of rhesus monkey preproQRFP with that of human preproQRFP (GenPept Accession No. BAC98934), very high homology of 87% was found (119 of 136 residues identical), confirming that the nucleotide sequence of the cloned gene codes for rhesus monkey preproQRFP.

FIG. 2 shows a comparison between the amino acid sequences of monkey preproQRFP (SEQ ID NO: 6), human preproQRFP (SEQ ID NO: 11), mouse preproQRFP (SEQ ID NO: 12), rat preproQRFP (SEQ ID NO: 13) and bovine preproQRFP (SEQ ID NO: 14).

The nucleotide sequences of the primers used for this example are shown below.

```
                                              (SEQ ID NO: 27)
hQRFPF2:    ATAGGATCCTTGGTGAGTTGCGCTTGGCCACGTGTG (SEQ ID NO: 28)
hQRFPR1:    ACAGCGGCCGCGGCTGGGACGACCGAGGCTCCAAGACA (SEQ ID NO: 29)
T7:         TAATACGACTCACTATAGGG (SEQ ID NO: 30)
BGHreverse: GGAGCTGACACGGAAGAT (SEQ ID NO: 31)
hQRFP-1:    CATGCTGGCTGCAGATTCCG (SEQ ID NO: 32)
hQRFP-2:    TCACTGCCTTCGTCCTGCCT.
```

EXAMPLE 3

(Detection of Intracellular Calcium Ion Concentration Increasing Activity in Rhesus Monkey GPR103 Gene-expressing 293T Cells)

Twenty-four hours after seeding $1 \times 10^6$ 293T cells in a 6-cm culture plate, they were transfected with pEF1/V5-HisB plasmid vector containing the rhesus monkey GPR103 gene obtained in Example 1 or the same vector without the insert (mock), using Lipofectamine 2000 (Invitrogen Corp.). For comparison, cells transfected with the same vector containing known human GPR103 cDNA were also prepared.

After 24 hours of culturing, the cells were seeded in a 96-well poly-D-lysine coated black culture plate (Becton Dickinson) at $3 \times 10^4$ cells/well and cultured overnight. The cell medium was removed, and then a mixture of 4 µM Fluo4-AM (Molecular Probes) and 0.04% Pluronic acid (Molecular Probes) added to DMEM (Invitrogen Corp.) containing 10% fetal bovine serum (HyClone) was added prior to incubation at 37° C. for 1 hour. Next, a mixture of 20 mM HEPES (pH 7.4, Invitrogen Corp.) and 0.5% bovine serum albumin (Sigma Corp.) added to Hank's Balanced Salt Solution (HBSS) was prepared as an assay buffer. The cells were rinsed with the assay buffer, and after removal of the excess Fluo4, they were set in a FLIPR (Molecular Devices Corp.).

Different concentrations of human QRFP43 (SEQ ID NO: 51) dissolved in the assay buffer were also set in the FLIPR, and then a sample was added to the cells and the change in intracellular calcium ion concentration-dependent fluorescence produced by irradiation with exciting light was measured.

Defining the change in fluorescence as the difference between the fluorescence immediately before addition of the peptide due to human QRFP43 and the maximum value after addition, a Prism Version 4.00 (GraphPad) was used to graph the change in fluorescence due to each concentration of peptide, and the 50% effective concentration was determined (FIG. 3).

As a result, it was found that human QRFP43 increased the intracellular calcium ion concentration of the rhesus monkey GPR103 gene-expressing 293T cells in a concentration-dependent manner, with a 50% effective concentration of 39 nM. The 50% effective concentration for intracellular calcium concentration increasing activity of human QRFP43 was 97 nM with the simultaneously observed human GPR103-expressing cells. On the other hand, no change in intracellular calcium ion concentration was seen by human QRFP43 in the cells transfected with the mock vector.

Thus, it was demonstrated that rhesus monkey GPR103 exhibits the property of a QRFP receptor similar to known human GPR103.

Example 4

(Isolation of Gene Homologous to Rat GPR 103 Gene)

The nucleotide sequence of the rat GPR103 gene (GenBank Accession No. NM_198199) was used as the query for a homology search on the Celera rat genome database using the BLAST algorithm, and a genetic sequence with homology to the rat GPR103 gene was found and designated as GPR103b.

The sequence from the Celera database was used as the basis to design two oligo DNA primers rBG29LF1 (SEQ ID NO: 33) and rBG29LR4 (SEQ ID NO: 34). The mRNA was purified from rat hypothalamus tissue using a FastTrack 2.0 mRNA Separation Kit (Invitrogen Corp.), and a SuperScript III: First Strand Synthesis System (Invitrogen Corp.) was used to synthesize cDNA.

The cDNA was used as template with the primers for PCR reaction comprising 40 cycles each consisting of 94° C., 10 seconds (denaturing reaction)/68° C., 1 min 30 seconds (annealing and extension reaction). The obtained PCR amplification product was digested with restriction endonucleases BamHI and NotI, and cloned in pEF1/V5-HisB plasmid vector (Invitrogen Corp.).

Four clones were randomly selected from among clones obtained by four independent PCR reactions, and the eight primers T7, BGHreverse, rQRFP2R-1, rQRFP2R-2, rQRFP2R-3, rQRFP2R-4, rQRFP2R-5 and rQRFP2R-6 (SEQ ID NOS: 35-42) were used to determine the nucleotide sequences by the dye terminator method.

A consensus sequence obtained by comparison of the nucleotide sequences of the four clones was 100% identical to the sequence from the Celera database.

The rat GPR103b gene has a 1245 base open reading frame (bases 1 to 1245). The amino acid sequence (415 residues) predicted from the open reading frame is listed as SEQ ID NO: 4.

Upon comparing the amino acid sequence of the rat GPR103b gene with that of human GPR103 (GenPept Accession No. BAC98938), high homology of 83% was found, confirming that rat GPR103b is a receptor for P518/QRFP (FIG. 1). Also, mouse TGR346b (GenPept Accession No. CAD82895) of known sequence has high amino acid sequence homology of 94% with rat GPR103b (392 of 416 residues identical), whereby it was further confirmed that rat GPR103b is a receptor for QRFP.

The nucleotide sequences of the primers used were as follows.

```
                                            (SEQ ID NO: 33)
rBG29LF1:   ATAGGATCCGGTCAAGGCGCCTACCGAACCCAGCATG (SEQ ID NO: 34)
rBG29LR4:   ACAGCGGCCGCAACAGGTCCTCATTCTGAAGACAC (SEQ ID NO: 35)
T7:         TAATACGACTCACTATAGGG (SEQ ID NO: 36)
BGHreverse: GGAGCTGACACGGAAGAT (SEQ ID NO: 37)
rQRFP2R-1:  TCACCTTCTTCTGCATTCCC (SEQ ID NO: 38)
rQRFP2R-2:  AAAATCTACACCACCTTCAT (SEQ ID NO: 39)
rQRFP2R-3   GCATGGAAGCTTGGGAGCCA (SEQ ID NO: 40)
rQRFP2R-4:  CCCCCAAATGCTTCCCCTTT (SEQ ID NO: 41)
rQRFP2R-5:  AGCTCATAACCGATTTTCCC (SEQ ID NO: 42)
rQRFP2R-6:  ATGAGCAGGTCGCTGAGTGCCA.
```

Example 5

(Detection of Intracellular Calcium Ion Concentration Increasing Activity in Rat GPR103b Gene-expressing 293T Cells)

Twenty-four hours after seeding 1×10$^6$ $^{293}$T cells in a 6-cm culture plate, they were transfected with pEF1/V5-HisB plasmid vector carrying the rat GPR103b gene obtained in Example 4 or the same vector without the insert (mock), using Lipofectamine 2000 (Invitrogen Corp.). There were also prepared cells transfected with the same vector containing cDNA of mouse GPR103b (having high homology to rat GPR103b, as shown in FIG. 1).

After 24 hours of culturing, the cells were seeded in a 96-well poly-D-lysine coated black culture plate (Becton Dickinson) at 3×10$^4$ cells/well and cultured overnight. The cell medium was removed, and then a mixture of 4 μM Fluo4-AM (Molecular Probes) and 0.04% Pluronic acid (Molecular Probes) added to DMEM (Invitrogen Corp.) containing 10% fetal bovine serum (HyClone) was added prior to incubation at 37° C. for 1 hour. Next, a mixture of 20 mM HEPES (pH 7.4, Invitrogen Corp.) and 0.5% bovine serum albumin (Sigma Corp.) added to Hank's Balanced Salt Solution (HBSS) was prepared as an assay buffer. The cells were rinsed with the assay buffer, and after removal of the excess Fluo4, they were set in a FLIPR (Molecular Devices Corp.). Different concentrations of human QRFP43 (SEQ ID NO: 51) dissolved in the assay buffer were also set in the FLIPR, and then a sample was added to the cells and the change in intracellular calcium ion concentration-dependent fluorescence produced by irradiation with exciting light was measured.

Figure 4:
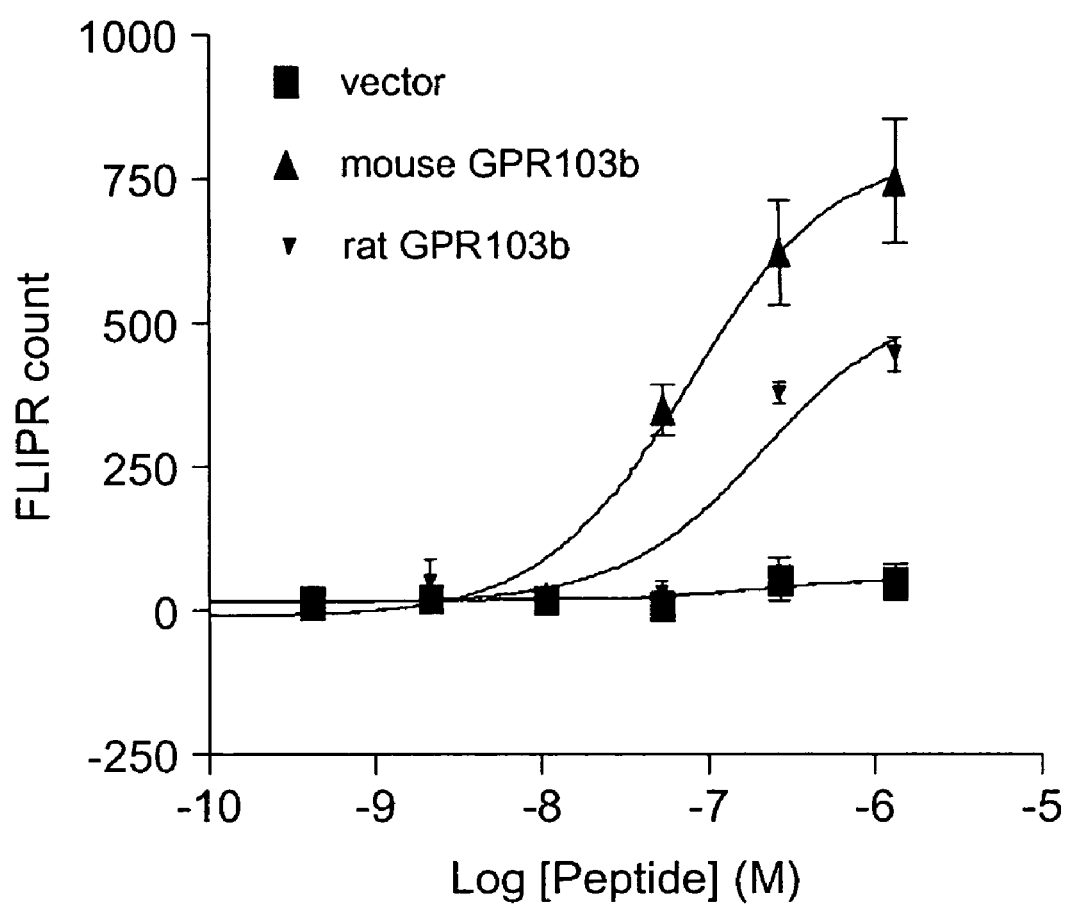
FIG. 4 is a graph showing intracellular calcium ion concentration increasing activity exhibited by different concentrations of QRFP for mouse and rat GPR103b-expressing 293T cells.

Defining the change in fluorescence as the difference between the fluorescence immediately before addition of the peptide due to human QRFP43 and the maximum value after addition, a Prism Version 4.00 (GraphPad) was used to graph the change in fluorescence due to each concentration of peptide, and the 50% effective concentration was determined (FIG. 4).

As a result, it was found that human QRFP43 increased the intracellular calcium ion concentration of the rat GPR103b gene-expressing 293T cells in a concentration-dependent manner, with a 50% effective concentration of 217 nM. The 50% effective concentration for intracellular calcium concentration increasing activity of human QRFP43 was 76 nM with the simultaneously observed mouse GPR103b-expressing cells. On the other hand, no change in intracellular calcium ion concentration was seen by human QRFP43 in the cells transfected with the mock vector. Thus, it was demonstrated that rat GPR103b and mouse GPR103b each exhibit the property of a QRFP receptor.

Example 6

(Synthesis of Monkey QRFP43 and QRFP26)

It is a publicly known fact that preproQRFP undergoes processing, involving C-terminal amidation and N-terminal pyroglutamylation. Monkey preproQRFP is also predicted to undergo processing at locations corresponding to QRFP of other species. The peptide produced by processing of monkey preproQRFP listed as SEQ ID NO: 6 was designated as monkey QRFP43 (SEQ ID NO: 49). It is also known that sufficient agonist activity against GPR103 is exhibited only by the portion corresponding to 26 amino acids from the C-terminus of human QRFP. It was predicted that monkey QRFP would also exhibit sufficient agonist activity at the portion corresponding to 26 amino acids from the C-terminus, and the corresponding peptide was designated as monkey QRFP26 (SEQ ID NO: 50).

For synthesis of the monkey QRFP43 and QRFP26, NovaSyn™ TGR resin sold by Novabuochem Co. was used as the starting material for each for condensation by the Fmoc method using a Pioneer™ Peptide Synthesizer with HATU as the condensation reagent, and after adding TFA/thioanisole/ethandithiol/m-cresol (95/2.5/1.5/1) to the obtained resin and shaking at room temperature for 1 hour and 30 minutes, the resin was filtered out. Cooled ether was added to the filtrate and there were obtained as precipitates crude Pyr-Asp-Glu-Gly-Ser-Glu-Ala-Asp-Asp-Phe-Leu-Pro-Ala-Gly-Gly-Val-Lys-Ala-Ser-Gly-Pro-Leu-Gly-Asn-Leu-Ala-Glu-Glu-Leu-Asn-Gly-Tyr-Ser-Arg-Lys-Lys-Gly-Gly-Phe-Ser-Phe-Arg-Phe-NH$_2$ (QRFP43) and crude Ala-Ser-Gly-Pro-Leu-Gly-Asn-Leu-Ala-Glu-Glu-Leu-Asn-Gly-Tyr-Ser-Arg-Lys-Lys-Gly-Gly-Phe-Ser-Phe-Arg-Phe-NH$_2$ (QRFP26). The crude peptides were purified by reverse-phase preparative HPLC using a YMC-Pack ODS-AQ, S-5, 120A column (20×250 mm) (Solution A: 0.1% TFA water, Solution B: 0.1% TFA acetonitrile, A/B: 95/5, 2 min, 73/27-58/42, 15 min linear concentration gradient elution, flow rate: 10 ml/min), and the fraction containing the target product was recovered and freeze-dried to obtain the target product.

Example 7

(Detection of Intracellular Calcium Ion Concentration Increasing Activity in Monkey GPR103 or Human GPR103 Gene-expressing CHO Cells upon Stimulation with Monkey QRFP43 or QRFP26) CHO cells were transfected with pEF1/V5-HisB plasmid vector carrying the monkey GPR103 gene or human GPR103 gene obtained in Example 1 and the same vector without the insert (mock), and Geneticin (Invitrogen Corp.) was added to the medium to a final concentration of 2 mg/ml for selection of expressing cells. Next, the monkey or human GPR103 gene-expressing cells were singly cloned by the limiting dilution method and supplied for the following test. The monkey QRFP43 and QRFP26 synthesized by the method described in Example 6 were also supplied for the test.

After 24 hours of culturing, the cells were seeded in a 96-well poly-D-lysine coated black culture plate (Becton Dickinson) at $2.5 \times 10^4$ cells/well and cultured for two nights. The cell medium was removed, and then a mixture of 4 µM Fluo4 AM (Molecular Probes), 0.04% Pluronic acid (Molecular Probes) and 2.5 mM Probenecid (Sigma Corp.) added to DMEM/F-12 (Invitrogen Corp.) containing 10% fetal bovine serum (Sigma Corp.) was added prior to incubation at 37° C. for 1 hour. Next, a mixture of 20 mM HEPES (Sigma Corp.), 2.5 mM Probenecid (Sigma Corp.) and 0.5% bovine serum albumin (Sigma Corp.) added to Hank's Balanced Salt Solution (HBSS) was adjusted to pH 7.4 with aqueous sodium hydroxide and prepared as an assay buffer. The cells were rinsed with the assay buffer, and after removal of the excess Fluo4, they were set in a FLIPR (Molecular Devices Corp.). Different concentrations of monkey QRFP43 or QRFP26 dissolved in the assay buffer were also set in the FLIPR, and then a sample was added to the cells and the change in intracellular calcium ion concentration-dependent fluorescence produced by irradiation with exciting light was measured.

Defining the change in fluorescence as the difference between the fluorescence immediately before addition of monkey QRFP43 or QRFP26 and the maximum value after addition, a Prism Version 4.00 (GraphPad) was used to graph the change in fluorescence due to each concentration of peptide (protein), and the 50% effective concentration was determined.

Figure 5:
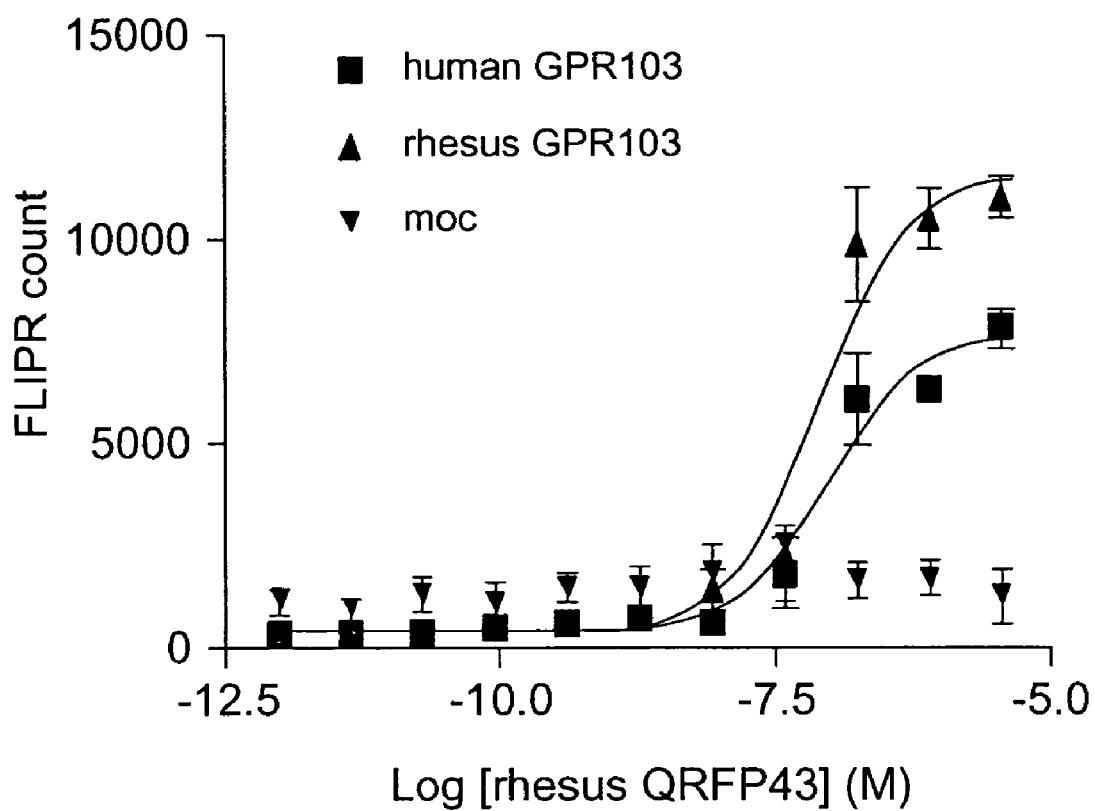
FIG. 5 is a graph showing intracellular calcium ion concentration increasing activity in monkey GPR103 or human GPR103 gene-expressing CHO cells upon stimulation with monkey QRFP43.
Figure 6:
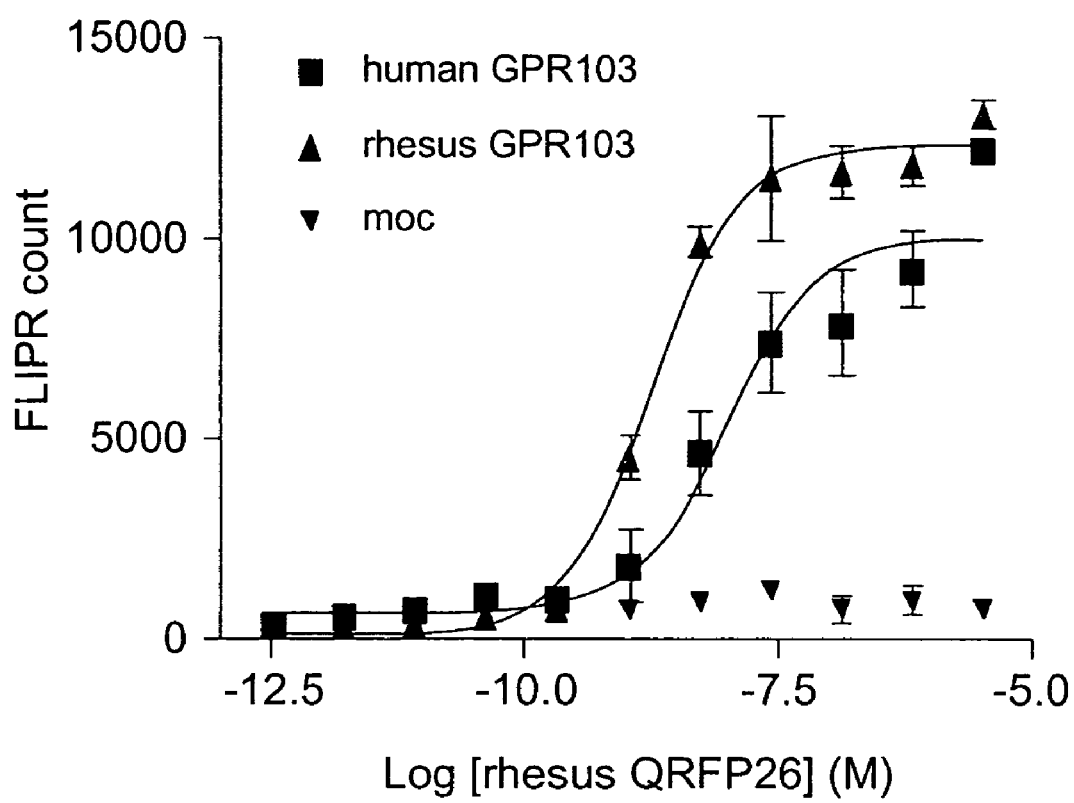
FIG. 6 is a graph showing intracellular calcium ion concentration increasing activity in monkey GPR103 or human GPR103 gene-expressing CHO cells upon stimulation with monkey QRFP26.

As a result, it was found that the monkey QRFP43 increased the intracellular calcium ion concentration of the monkey and human GPR103 gene-expressing CHO cells in a concentration-dependent manner, with 50% effective concentrations of 69 nM and 58 nM, respectively (FIG. 5). The 50% effective concentrations for intracellular calcium ion concentration increasing activity of the simultaneously measured monkey QRFP26 were 9.2 nM for the monkey GPR103 gene-expressing CHO cells and 1.7 nM for the human GPR103 gene-expressing CHO cells (FIG. 6). However, no change in intracellular calcium ion concentration by either monkey QRFP was seen in the cells transfected with the mock vector (FIGS. 5 and 6).

Thus, it was demonstrated that monkey QRFP43 and QRFP26 each exhibit the property of a GPR103 agonist.

Example 8

(Administration of Human QRFP43 to Rats and Mice)

QRFP was administered to SD rats and C57BL mice, and then food consumption was measured.

The SD rats (9- to 12-week-old) were anesthetized, and a guide cannula (26 gauge) was inserted into the third cerebral ventricle and anchored with dental resin. The position of the guide cannula was 2.2 mm behind the bregma and 8 mm deep from the cranial surface on the median line.

The C57BL mice (9- to 12-week-old) were anesthetized, and a guide cannula (27 gauge) was inserted into the lateral cerebral ventricle and anchored with dental resin. The position of the guide cannula was 0.4 mm behind and 0.8 mm to the right of the bregma, and 1 mm deep from the cranial surface.

After a recovery period of about two weeks, an inner needle (33 gauge) connected to a microsyringe was inserted into the guide cannula, and QRFP dissolved in artificial cerebrospinal fluid (100 micrograms/head for rat and 10 or 30 micrograms/head for mouse) was administered into the cerebral ventricle, after which food consumption was measured for 2 hours.

Figure 7:
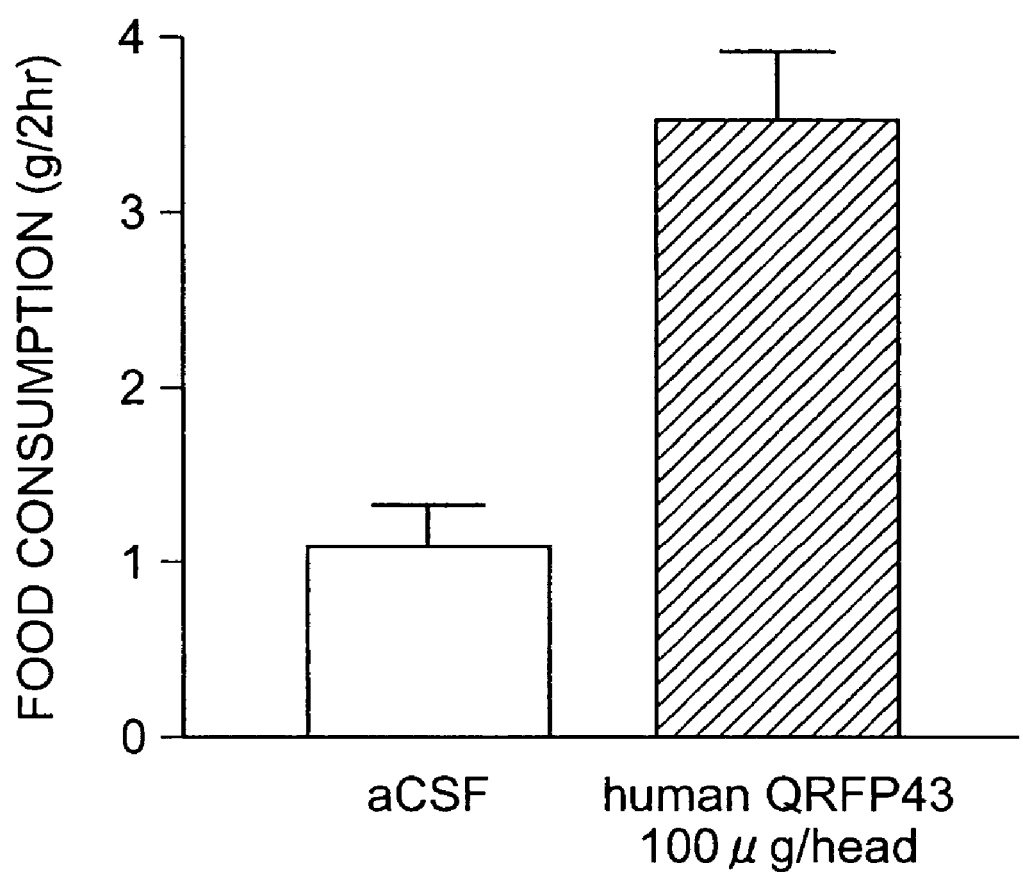
FIG. 7 is a bar graph showing food consumption two hours after administration of QRFP to the third cerebral ventricle of rats.
Figure 8:
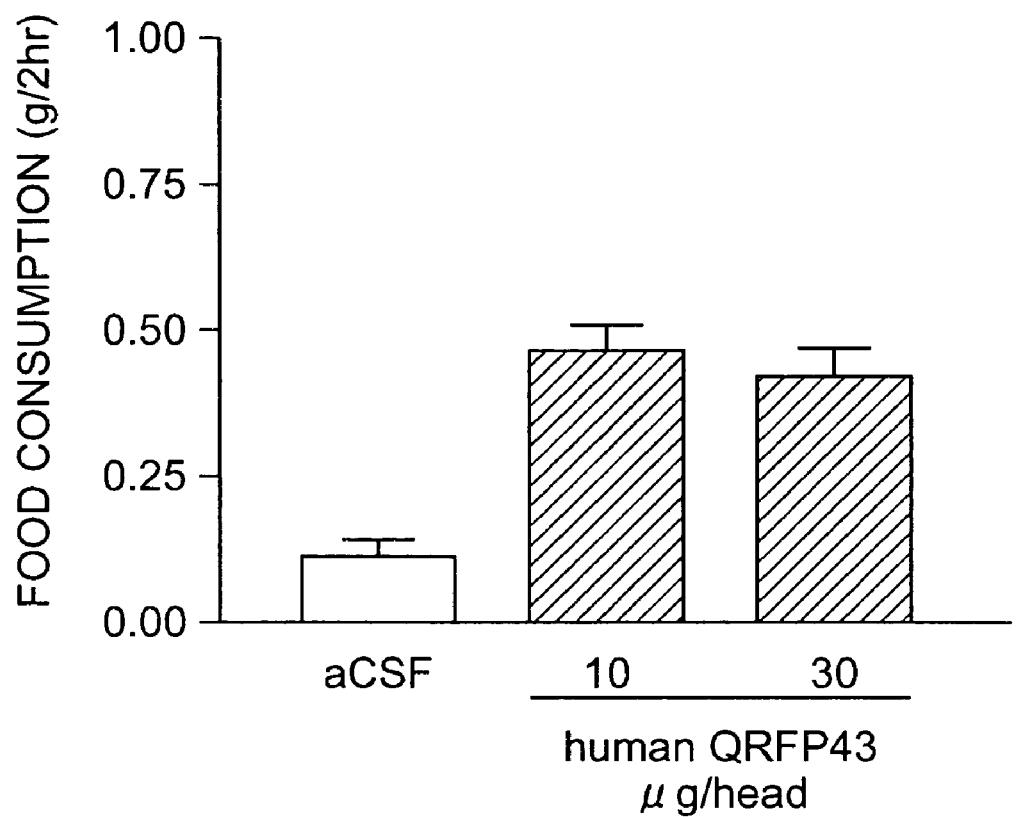
FIG. 8 is a bar graph showing food consumption two hours after administration of QRFP to the lateral cerebral ventricle of mice.

FIG. 7 shows food consumption 2 hours after administration of human QRFP43 to the third cerebral ventricle of the rats, and FIG. 8 shows food consumption 2 hours after administration of human QRFP43 to the lateral cerebral ventricle of the mice. As shown in FIGS. 7 and 8, the food consumption after administration in the administered animals was significantly increased compared to animals not administered QRFP. Thus, it was confirmed that QRFP and its receptor GPR103 are involved in regulating food consumption. Food consumption with administration of the artificial cerebrospinal fluid (aCSF) alone without QRFP was used as reference.

The t-test was used in the rat experiment, and a significant difference was found (p<0.001). ANOVA followed by Bonferroni/Dun was used in the mouse experiment, and a significant difference (p<0.01) was found in all of the QRFP-administered groups compared to the artificial cerebrospinal fluid-administered group.

Example 9

(Expression of GPR103 and QRFP in ob/ob Mice)

The hypothalamus was extracted from each of fourteen ob/ob mice and ten C57BL/6J mice, ISOGEN (Nippon Gene Co., Ltd.) was used for extraction of the total RNA, and Reverse Transcription Reagents (Applied Biosystems Japan, Ltd.) was used for synthesis of cDNA. A 100 µl portion of reverse transcription reaction solution contains random hexamers and 2 µl of total RNA. A negative control was also prepared having the same composition as the reverse transcription reaction solution but without the reverse transcriptase.

Detection and quantitation of the mouse GPR103 and mouse preproQRFP mRNA were carried out by real-time quantitative PCR (according to the manual with an ABI PRISM 7900HT Sequence Detection System (Applied Biosystems Japan, Ltd.)). The primers and probes used were the following.

```
mGPR103F:
TCTTTGGCAACTCTCTGGTCATC    (SEQ ID NO: 43)

mGPR103R:
CAGAAGAAGGCAATGAGCAGATC    (SEQ ID NO: 44)

mGPR103T:
TGCGCACCGTCACCAACATCTTC    (SEQ ID NO: 45)

mQRFPF:
TCTCCCTCTGAGTGCCTGCT       (SEQ ID NO: 46)

mQRFPR:
GCCTGTGCTGTGGATTTTGA       (SEQ ID NO: 47)

mQRFPT:
CAGACATCGGTGACATCGGAGCCA.  (SEQ ID NO: 48)
```

For quantitation of GPR103 mRNA there were used both primers mGPR103F and mGPR103R and the FAM-labeled probe mGPR103T. For quantitation of preproQRFP mRNA there were used both primers mQRFPF and mQRFPR and the FAM-labeled TaqMan probe mQRFPT. Beta-actin was used as an internal standard (FEBS Lett. 2001 Sep. 7; 505(1):136-40).

A TaqMan Universal PCR master mix (Applied Biosystems Japan, Ltd.) was used to prepare a 10 µl reaction mixture containing 900 nM of each primer, 250 nM of each TaqMan probe and 0.25 µl of the previously synthesized cDNA. This mix contains TaqMan probes and primers for quantitation of beta-actin, as well as TaqMan probes and primers for quantitation of GPR103 or preproQRFP. The relative amount of actin was calculated using a calibration curve.

Figure 9:
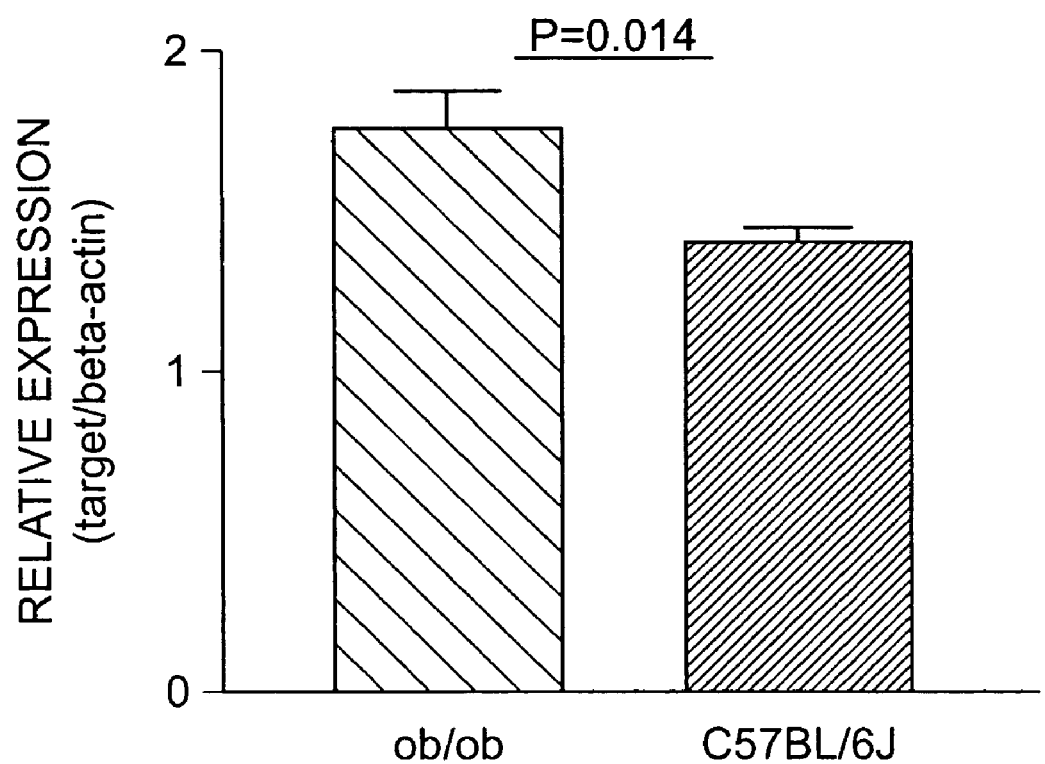
FIG. 9 is a bar graph showing expression of GPR103 in ob/ob mice.
Figure 10:
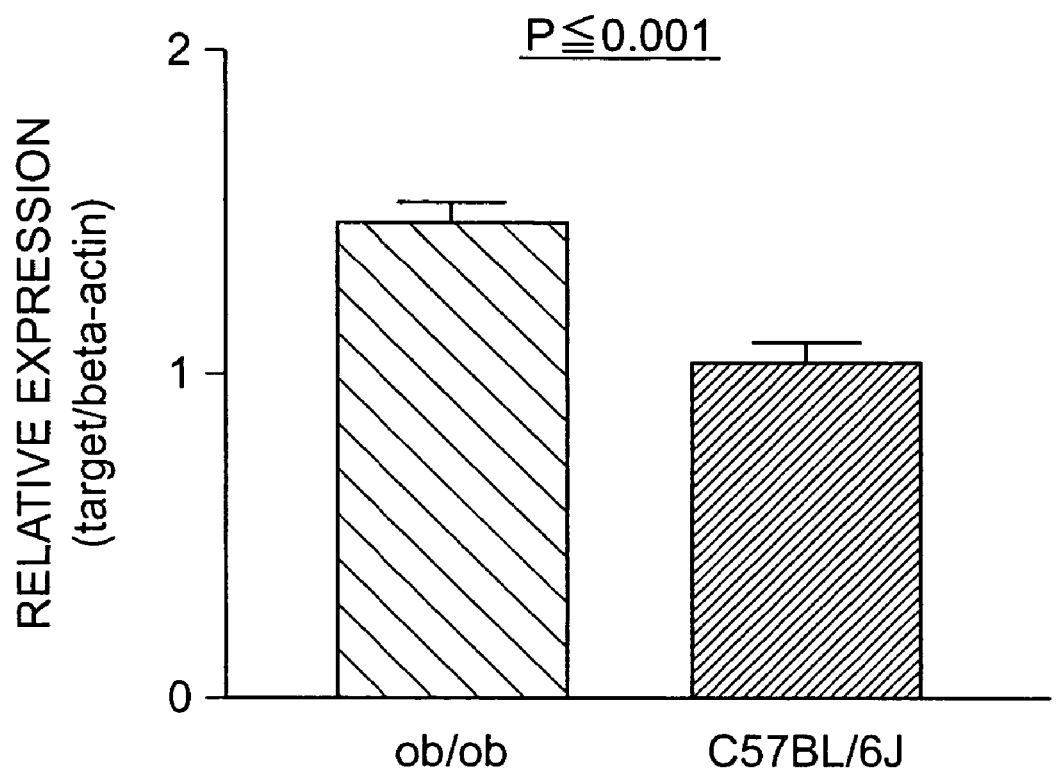
FIG. 10 is a bar graph showing expression of QRFP in ob/ob mice.

The results, shown in FIGS. 9 and 10, demonstrate that increased expression of GPR103 and preproQRFP mRNA was observed in the hypothalamus of ob/ob mice compared to the normal C57BL/6J mice. It is widely known that ob/ob mice are leptin-deficient and exhibit obesity and hyperphagia. In other words, it was suggested that leptin acts in an inhibitory manner on GPR103 and preproQRFP expression. It was also concluded that GPR103 and preproQRFP are closely involved in eliciting the obesity and hyperphagia associated with leptin deficiency.

INDUSTRIAL APPLICABILITY

As explained above, the GPR103 of the invention and the compound evaluation method employing it can yield information relating to non-human primate and rat GPR103 genes and proteins and their sequences, and permit construction of GPR103 model systems as targets for human drugs. Moreover, the compound evaluation method of the invention permits evaluation and development of compounds as therapeutic and diagnostic agents for diseases associated with physiological function of GPR103.

The invention claimed is:

1. An isolated nucleic acid comprising SEQ ID NO: 1.

2. An isolated nucleic acid coding for a protein comprising SEQ ID NO: 2.

3. An expression vector comprising the nucleic acid according to claim 1.

4. An isolated host cell comprising the expression vector according to claim 3.

* * * * *